United States Patent
West et al.

(10) Patent No.: US 12,023,663 B2
(45) Date of Patent: Jul. 2, 2024

(54) RETAINING TABLE FOR FLUID PROCESSING SYSTEM

(71) Applicant: Fenwal, Inc., Lake Zurich, IL (US)

(72) Inventors: Richard L. West, Lake Villa, IL (US); Alexandra Salomon, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 312 days.

(21) Appl. No.: 17/522,341

(22) Filed: Nov. 9, 2021

(65) Prior Publication Data

US 2022/0143620 A1    May 12, 2022

Related U.S. Application Data

(60) Provisional application No. 63/111,954, filed on Nov. 10, 2020.

(51) Int. Cl.
| | |
|---|---|
| *B01L 3/00* | (2006.01) |
| *C12M 1/00* | (2006.01) |
| *C12M 1/12* | (2006.01) |
| *C12M 3/00* | (2006.01) |

(52) U.S. Cl.
CPC ............ *B01L 13/00* (2019.08); *B01L 3/56* (2013.01); *C12M 23/14* (2013.01); *C12M 23/28* (2013.01); *C12M 23/48* (2013.01); *C12M 37/00* (2013.01); *B01L 2200/0647* (2013.01); *B01L 2300/043* (2013.01); *B01L 2300/045* (2013.01); *B01L 2300/123* (2013.01)

(58) Field of Classification Search
CPC ...... B01L 13/00; B01L 3/56; B01L 2300/043; B01L 2300/045; B01L 2300/123; B01L 2200/0647; C12M 23/14; C12M 23/28; C12M 23/48; C12M 37/00

USPC ................................................. 108/27, 50.18
See application file for complete search history.

(56) References Cited

U.S. PATENT DOCUMENTS

| | | | | |
|---|---|---|---|---|
| 1,290,072 A | * | 1/1919 | Bullock ................. | A47B 23/02 108/27 |
| 2,056,791 A | * | 10/1936 | Logan .................... | G01N 21/29 356/246 |
| 2,088,077 A | * | 7/1937 | Wood ..................... | A47F 5/005 312/140.3 |
| 2,778,703 A | * | 1/1957 | McBride ................ | F16B 12/28 312/140.1 |
| 3,916,802 A | * | 11/1975 | Virtue .................... | A47D 5/00 5/655 |
| 4,495,150 A | * | 1/1985 | Cook ...................... | B01L 13/02 422/549 |

(Continued)

FOREIGN PATENT DOCUMENTS

WO        WO 93/00937        1/1993

OTHER PUBLICATIONS

Extended European Search Report for EP 21207055.1 dated Mar. 15, 2022; 8 pages.

*Primary Examiner* — Jose V Chen
(74) *Attorney, Agent, or Firm* — Cook Alex Ltd.

(57) ABSTRACT

A retaining table for use with a fluid processing system includes a plate having a generally flat top surface with opposed first and second ends and opposed first and second lateral edges for supporting a disposable container, a first retaining structure connected to the plate along the first end, and a second retaining structure connected to the plate along the second end.

32 Claims, 17 Drawing Sheets

(56) References Cited

U.S. PATENT DOCUMENTS

| | | | | |
|---|---|---|---|---|
| 5,018,628 A * | 5/1991 | Schenck | A47B 96/18 | |
| | | | 312/140.3 | |
| 5,127,537 A * | 7/1992 | Graham | G01N 1/36 | |
| | | | 220/838 | |
| 6,023,800 A * | 2/2000 | Stickley | A61G 7/0507 | |
| | | | 5/503.1 | |
| 6,671,904 B2 * | 1/2004 | Easterling | F16M 13/02 | |
| | | | 5/601 | |
| 8,322,290 B1 * | 12/2012 | Mignano | A47B 23/043 | |
| | | | 248/456 | |
| 8,782,832 B2 * | 7/2014 | Blyakher | A61B 6/0421 | |
| | | | 5/624 | |
| 2003/0214874 A1 | 11/2003 | Hlavinka et al. | | |
| 2004/0223890 A1 * | 11/2004 | Summers | B01L 9/52 | |
| | | | 422/400 | |
| 2007/0098601 A1 * | 5/2007 | Mabuchi | B01L 3/50853 | |
| | | | 422/400 | |
| 2007/0116612 A1 * | 5/2007 | Williamson | A61B 10/0096 | |
| | | | 422/400 | |
| 2011/0048288 A1 * | 3/2011 | Sheldon | B25H 1/04 | |
| | | | 108/50.18 | |
| 2014/0345499 A1 * | 11/2014 | Wilson | A47D 1/0081 | |
| | | | 108/50.11 | |
| 2015/0059622 A1 * | 3/2015 | Quinones | A47B 97/00 | |
| | | | 108/27 | |
| 2015/0063056 A1 | 3/2015 | Kral et al. | | |
| 2016/0271612 A1 * | 9/2016 | Masoumi | C12M 23/50 | |
| 2018/0154289 A1 * | 6/2018 | Rhodes | C12M 23/14 | |
| 2018/0156701 A1 * | 6/2018 | Williamson, IV | G01N 1/06 | |
| 2019/0336706 A1 | 11/2019 | Shavit et al. | | |
| 2019/0342946 A1 * | 11/2019 | Shavit | A01N 1/0242 | |
| 2020/0060661 A1 * | 2/2020 | Goeckner | B01L 3/508 | |
| 2020/0298241 A1 * | 9/2020 | Kabaha | B01L 3/5085 | |
| 2021/0205817 A1 * | 7/2021 | Bonnoitt, Jr. | B01L 3/0275 | |
| 2021/0308666 A1 * | 10/2021 | Chou | G01N 21/01 | |
| 2023/0068002 A1 * | 3/2023 | Yang | A61B 5/0004 | |
| 2023/0358739 A1 * | 11/2023 | Van Workum | G01N 33/54386 | |

\* cited by examiner

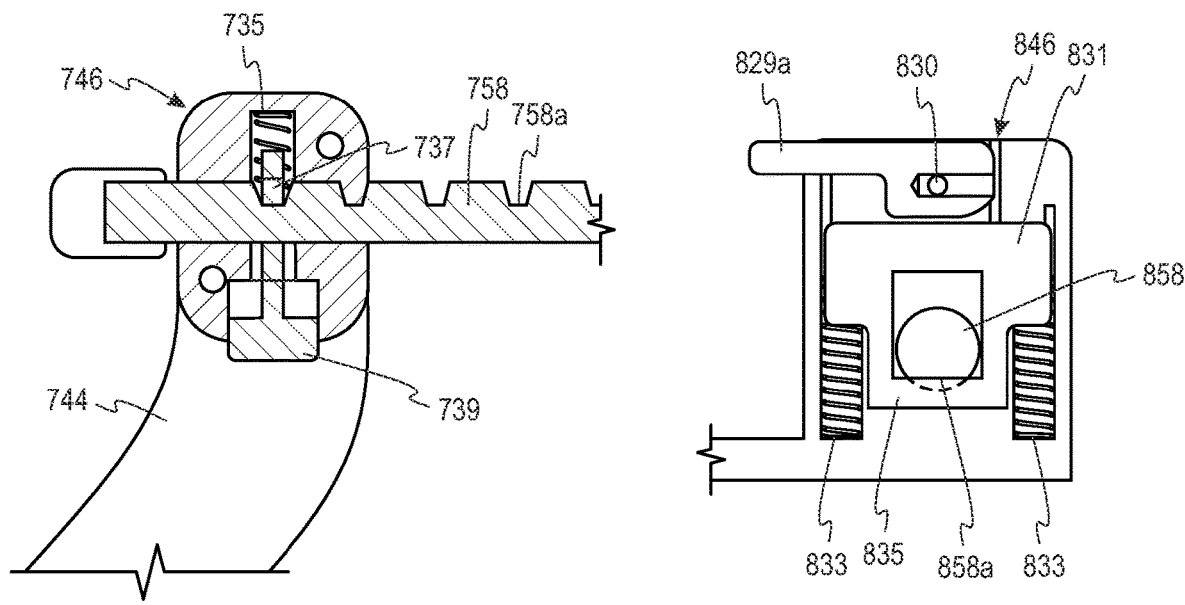
Fig. 12
Fig. 14
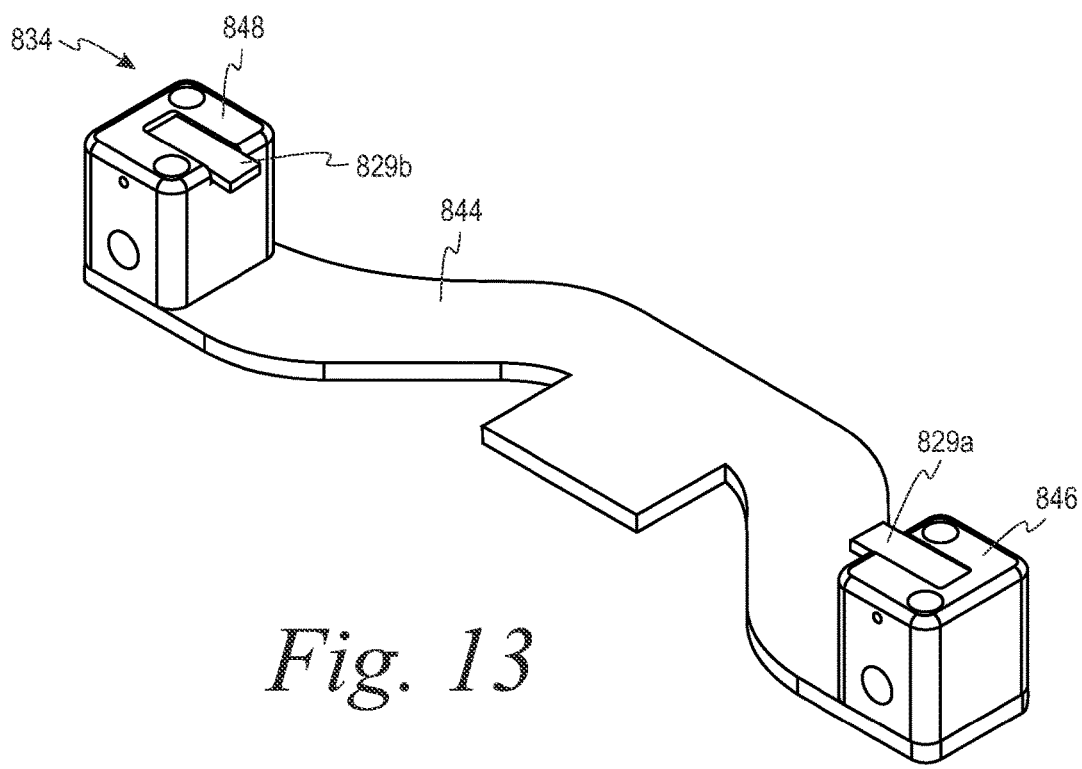
Fig. 13

RETAINING TABLE FOR FLUID PROCESSING SYSTEM

CROSS-REFERENCE TO RELATED APPLICATION

This application claims the benefit of U.S. Provisional Application No. 63/111,954, filed Nov. 10, 2020, which is incorporated herein by reference in its entirety.

TECHNICAL FIELD

The present disclosure is generally directed to retaining means for fluid processing systems. More particularly, the present disclosure is directed to a retaining table for fluid processing systems.

BACKGROUND

A number of well-known therapies are currently practiced in which a targeted cellular blood component (e.g., red blood cells, white blood cells, and platelets) is separated from whole blood and stored for later infusion to a patient. The targeted cell product (e.g., red blood cells, white blood cells, or platelets) may be in a suspension that includes plasma and/or some other supernatant. As such, it is sometimes desirable to "wash" the cellular suspension (typically with a physiologic buffer) to remove the plasma/supernatant, as well as any non-target cellular material, prior to reinfusion. Systems and methods for cell washing are exemplified by U.S. Publication Nos. 2013/0341291, 2013/0092630, 2014/0199680, and 2021/0046426, each of which is incorporated herein by reference. Each of these published applications discloses cell washing methods utilizing a disposable fluid circuit including a spinning membrane separator and a reusable processing machine.

Fluid processing systems for washing these cellular suspensions may require simultaneous mixing and cooling or heating, various measurements or other manipulation of cell products, which typically are housed in a disposable container, such as a bag. The disposable containers and/or bags may come in different sizes and designs depending on the source, cell type, and user's processes. There may be a wide variety container or bag features to be accommodated, such as: bag size and shape; bag material and texture; retaining holes or slots size, shape or location; material, size or location of tubing extending from the container or bag; and port types, material, size or location. No matter the variation, the wide variety of containers and/or bags need to be retained on a given system while being mixed and/or cooled or heated, or subject to measurements or other manipulation.

It may be desirable for the bag, while full or being filled with fluid, to be disposed on a table and mixed by movement, such as by rocking, orbital or vibratory movement. For example, rocking may provide oscillatory tilting, such as, up to approximately 30 degrees beyond horizontal in both directions. Thus, the constantly changing magnitude and direction of the forces associated with the bag to provide mixing may create sloshing, with a tendency for the bag to remove itself from the table. During fluid processing, liquid may be removed or added to the bag, also changing its shape. The bag may start empty and flat and become rounded, with the edges or seams lifting from the surface of the table during processing. If the table is configured to move, such as by rocking, orbital or vibratory motion, it is important to try to secure or retain the bag to prevent sliding, rolling or flipping and/or to maintain close contact with a cooling or heating element, or other measurement or cell manipulation equipment. It is therefore desirable to provide a retaining table which can adequately hold in place multiple bag types and secure the bags during mixing, cooling or heating, or measurements or alternative manipulation.

SUMMARY

Disposable kits for fluid processing may include a variety of disposable containers or bags, which typically are flexible, but may be semi-rigid. During fluid processing that includes positioning of a disposable container or bag on a retaining table that may be configured to move, the changing shape of the container during processing tends to require that only one edge of the container may be secured to the table. This may be necessary to avoid restraining the bag so much that it is not able to be filled and/or mixed.

The present disclosure provides example embodiments having advantageous retaining structures to retain a container on a retaining table during fluid processing that may include movement of the table, such as for mixing of fluid in the container. The retaining structures permit use of containers specifically designed for use with a particular fluid processing system, but also accommodate non-standard or customer defined containers, which may vary in design and construction. The retaining structures also provide for simple, intuitive and convenient use that permits a single user to quickly install and remove different containers from the retaining table. The structures also conveniently accommodate containers having various locations of ports and tubes extending therefrom. The retaining structures also recognize that, while a disposable container may be secured along only one edge, it is preferable that the edge having a tubing for drainage of the container will be the opposed edge, which is permitted to float or move while the container changes shape during filling or draining.

In a first aspect, a retaining table for use with a fluid processing system comprises a plate having a generally flat top surface with opposed first and second ends and opposed first and second lateral edges for supporting a disposable container, a first retaining structure connected to the plate along the first end, and a second retaining structure connected to the plate along the second end.

In a second aspect, a retaining table for use with a fluid processing system comprises a plate having a generally flat top surface with opposed first and second ends and opposed first and second lateral edges for supporting a disposable container, a door connected to the plate by at least one hinge along the first lateral edge and being movable between open and closed positions, and a latch along the opposed second lateral edge releasably retains the door in the closed position, and further comprising openings at the first and second ends of the plate or door configured for pass through of components extending from the disposable container.

In accordance with additional aspects, the table may be configured for movement and/or may include a temperature adjusting element, measurement or other manipulation apparatus. At least one retaining structure may be connected to the plate along at least one of the first and second lateral edges. Also, the first retaining structure may be adjustably connected to the plate to permit securing and centering of containers of varying length.

The novel and inventive structures disclosed herein provide for unique advantages in retaining disposable containers on a table used in fluid processing and may be used in various configurations to provide desired features for end users.

DESCRIPTION OF THE DRAWINGS

FIG. 12 is a schematic partial cross-sectional top view of a clamp device of the clamp system of FIG. 9.

FIG. 13 is a perspective view of a second embodiment of a clamp system for use with a retaining table, such as the table of FIG. 10.

FIG. 14 is a schematic partial cross-sectional side view of a clamp device of the clamp system of FIG. 13.

DETAILED DESCRIPTION

A more detailed description of the systems in accordance with the present disclosure is set forth herein. It should be understood that the description below of specific devices is intended to be exemplary, and not exhaustive of all possible variations or applications. Thus, the scope of the disclosure is not intended to be limiting and should be understood to encompass variations or embodiments that would occur to persons of ordinary skill.

Figure 1:
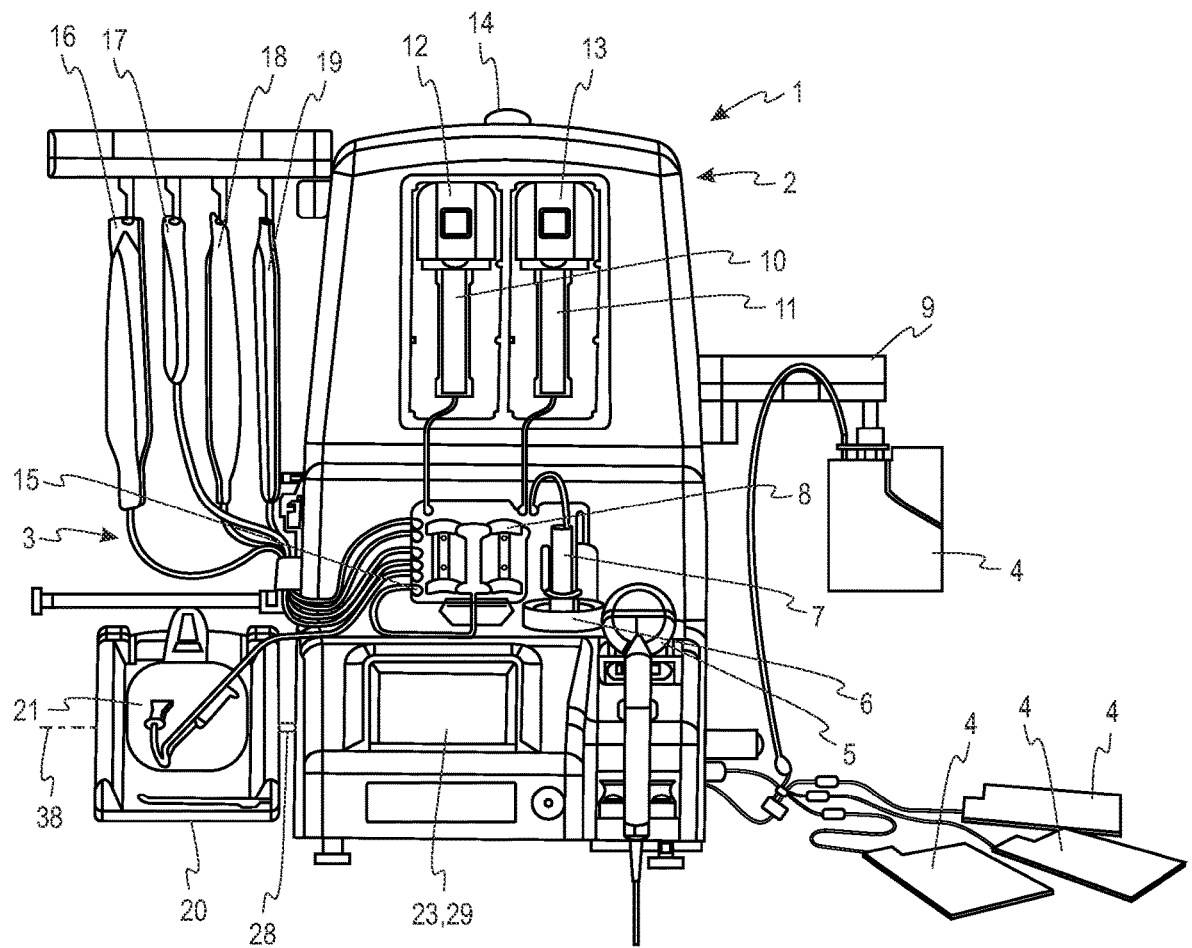
FIG. 1 is a perspective view of a system for fluid processing (e.g., including disposable fluid circuit components and a reusable processing machine or hardware).

Turning first to FIG. 1, an embodiment of a system 1 for processing fluids, such as cell suspensions (e.g., cell washing), is illustrated. The system 1 includes a disposable fluid circuit (also referred to as a set or kit) 3 and a reusable processing machine or reusable hardware 2.

As seen in FIG. 1, the disposable fluid circuit 3 is connectable to a source container 16 of fluid, in particular biological fluid. The disposable fluid circuit 3 includes a spinning membrane separator 7 that is used to process the fluid received from the source container 16, and to direct a portion of that fluid into one of more product containers 4. For example, the containers 4 may be in the form of flexible bags according to the illustrated embodiment. The flow of fluid from the source container 16, through the spinning membrane separator 7, and to the one or more product containers 4 is achieved through the use of first and second syringes 10, 11, which are in fluid communication with the source container 16, the spinning membrane separator (or spinning membrane for short) 7, and the one or more product containers 4. The syringes 10, 11 also may be in fluid communication with a number of other containers 17, 18, 19, 21.

The flow of fluid between the containers 4, 16, 17, 18, 19, and 21, the spinning membrane 7, and the syringes 10, 11 is controlled using a flow control cassette 15, which may be connected to each of the foregoing by tubing, or lines. In addition, the cassette 15 may include internal flow paths that are defined in part by a plurality of separate channels or passages, which in turn may be contained within and may be defined by the structure (e.g., housing) of the cassette 15. The channels may be connected at a plurality of selectable junctions, which may control the flow of fluid from one channel to another. These selectable junctions also may be referred to as valves, valve stations, or clamps, because the selectable junctions provide controlled access between the channels. The cassette 15 also may include sensor stations, by which sensors may be associated with the flow paths within the cassette 15 to determine characteristics of the flow therein, such as pressure, presence of air and/or fluid, or optical properties. Preferably, the length of each of the lines and channels is kept as short as possible to further minimize the internal volume of the fluid circuit 3.

The housing of the spinning membrane 7 and the syringes 10, 11 may be integrally formed as part of (i.e., as one piece with) the cassette 15, so as to further reduce the tubing volume associated with the kit 3. According to other embodiments, the spinning membrane 7 and/or the syringes 10, 11 may be attached to the remainder of the fluid circuit 3 at the time of use, as may be the case with one or more of the containers 4, 16, 17, 18, 19, 21. One or more of the containers 4, 16, 17, 18, 19 and 21 may be replaced with each use. The container 21 may, for example, be the final product bag (particularly where it is desired to collect as much final product as possible instead of collecting to a target weight).

As seen in FIG. 1, the reusable hardware 2 includes a drive 6 for the spinning membrane separator 7, a syringe pump 12, 13 for each respective syringe 10, 11, and a control cassette interface 8 that is associated with the flow control cassette 15 when the fluid circuit 3 is disposed on the hardware 2 (e.g., is mounted on the hardware 2). The cassette interface 8 includes actuators and sensors that are associated with the clamps and sensor stations of the flow control cassette 15 and are configured to operate the clamps or sense characteristics of the fluid, respectively.

The reusable hardware 2 also includes a controller (not shown) that is configured to control operation of the system 1. The controller may include a microprocessor (which, in fact may include multiple physical and/or virtual processors) and one or more electrical circuits and memories. The instructions by which the microprocessor is programmed may be stored on the one or more memories associated with the microprocessor. The memory/memories may include one or more tangible non-transitory computer readable memories, having computer executable instructions stored thereon, which when executed by the microprocessor, may cause the microprocessor to carry out one or more actions as described herein.

The controller may be coupled (i.e., directly or indirectly connected) to the equipment of the reusable hardware 2, such as the spinning membrane drive 6, the first syringe pump 12, the second syringe pump 13, and the cassette interface 8. The controller may operate each of these devices, each of which may be an assembly of other devices or equipment, to cause the fluid to flow through the fluid circuit 3 associated with the hardware 2, for example to cause fluid to flow from the source container 16, through the spinning membrane 7, and eventually into the product container(s) 4. The controller may be programmed to perform other actions as well, such as to test the fluid circuit 3, to prime the fluid circuit 3, to rinse parts of the disposable fluid circuit 3 after the wash has been performed, to add other components to the cell-containing fluid before that fluid is distributed to the product container(s) 4, and to distribute the cell-containing fluid into the product container(s) 4.

As illustrated, the embodiment of the system 1 includes a retaining table 20 on which the container 21 is disposed. The table 20 may be configured to be dynamic, such as to move, by being mounted on a motor-drive shaft 28 that permits the retaining table 20 to oscillate about an axis of rotation 38. The controller may control the table 20 (via a motor connected to the motor-drive shaft 28) to cause the retaining table 20 to rock or oscillate to agitate and mix the contents of the container 21 disposed on the table 20. It will be appreciated that oscillatory movement of the table may be provided by alternative drive means, or the table may be equipped to move in a different manner, such as via orbital or vibratory movement. While the table is shown directly connected to the fluid processing equipment, it will be appreciated that the retaining table may embody a stand-alone apparatus and may have a suitable drive system associated therewith.

The retaining table 20 also may include a temperature adjusting element for cooling or heating, which permits the material in the container 21 to be maintained at a particular temperature. Agitation and cooling may be important to quickly distribute and slow any chemical reaction in the contents of the container 21. Agitation also may force convection, removing temperature gradients within the contents and fully integrating the contents of the container 21. It will be appreciated that the table additionally or alternatively may include other apparatus along the top surface, such as measurement or other equipment used for diagnostic or other cellular manipulation purposes, wherein it is desirable to maintain close contact with the container during movement of the table.

According to the illustrated embodiment, the contents of the container 21 may be filled into one or more product containers 4 that are attached to the circuit 3. The system 10 may include a scale 9 for weighing the contents of the container(s) 4.

The system 1 may include other equipment as part of the reusable hardware 2, in addition to the equipment already discussed. For example, the system 1 may include a display 23 with touch screen 29 to permit information to be entered into the system, including information regarding the protocol of the procedure to be carried out by the system 1. The display 23 may be an electronic display, for example, with the touch screen 29 mounted thereon. Other input devices may be included, such as a pointer (e.g., mouse) and keyboard or keypad. Also, as illustrated in FIG. 1, an input device in the form of a barcode reader 5 may be attached to the system 1 to permit information to be inputted into the system 1 (and the controller) by scanning or reading a barcode, such as may be applied to the fluid circuit 3 or to one or more of the containers 4, 16, 17, 18, 19, 21. Other output devices also may be included, such as one or more lights (e.g., light emitting diodes or bulbs) 14, which may be used to signal alerts, events or machine states to the operator.

Further details as to the system 1 and its operation may be found in U.S. patent application Ser. No. 16/541,559, filed Aug. 15, 2019, incorporated herein by reference.

The above-described system 1 may require disposable containers 21 to be mixed and temperature adjusted or subject to measurements or other manipulation while on the retaining table 20. The container 21 ideally should be firmly secured, visible, and accessible. The present disclosure provides retaining means that advantageously center a disposable container on the surface of a table. The disposable containers 21 may be provided from a variety of sources, and the retaining structures disclosed herein are intuitive to use and adapt quickly and conveniently to a variety of container designs with possible aforementioned variations, such as in bag size, material, texture, hole or slot shapes, sizes and locations, and port or tubes connected thereto. A disposable container likely will include at least one or more tubes for draining and/or filling. During such draining and/or filling, the shape of the container also may change, which in turn may change the magnitude and direction of the load generated during oscillation. The tables and retaining structures disclosed herein therefore are highly advantageous by being adaptable and able to accommodate a large selection or variety of container or bag designs and structures.

The table 20 includes a plate having a generally flat top surface and includes at least one structure thereon for retaining a disposable container, and as such, may be referred to as a retaining table. Preferably, the plate includes structures, or retaining means, along each of the four sides for retaining a container or bag. However, it will be appreciated that it is within the scope of the present disclosure to have retaining structures along fewer than all of the sides of the plate, such as one, two or three structures along selected respective sides of the plate. It also will be appreciated that "sides" of the plate is a relative term in that the plate may not have straight or perpendicular edges. Moreover, the term "plate" will be understood herein to refer to a structure that provides a top of a table, whether it be a separately formed and connected component or an integrally formed portion at the top of the table.

Although specifically designated embodiments are disclosed, it is within the contemplation of the inventors and the scope of the present disclosure to combine elements, retaining structures or features from different embodiments herein. Also, similar or identical elements are numbered similarly throughout the different embodiments in the description and drawings.

Figure 2:
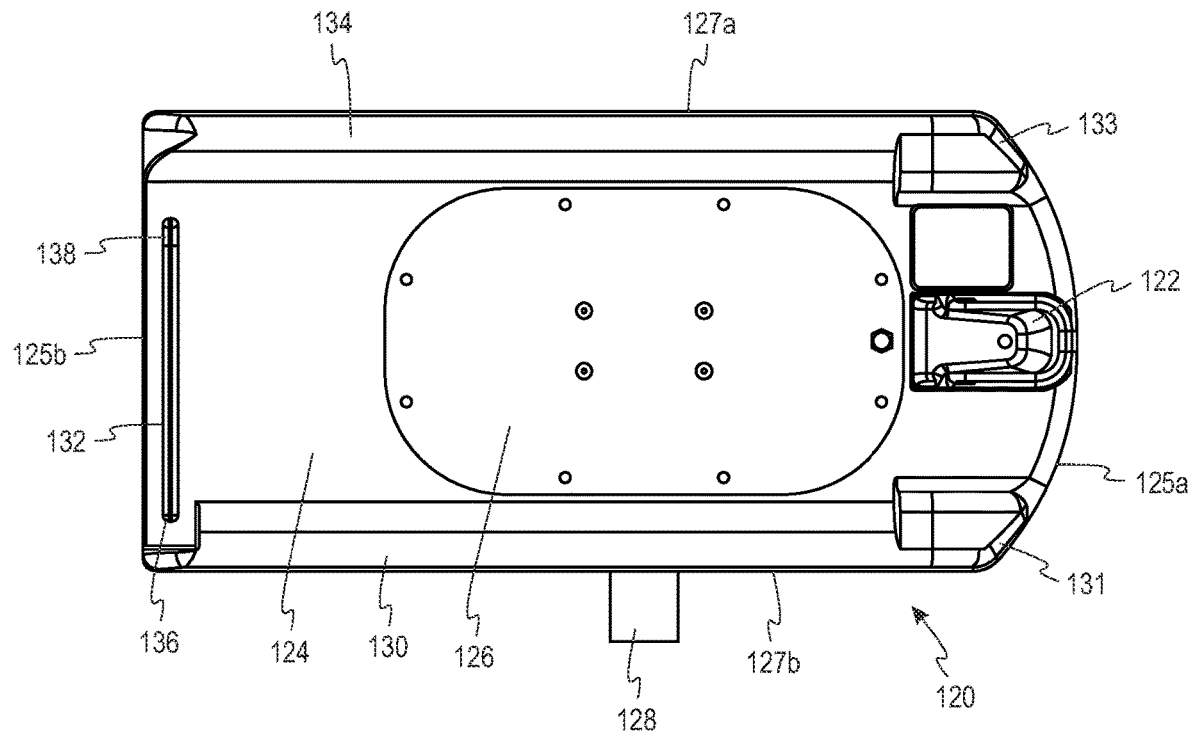
FIG. 2 is a top view of a first embodiment of a retaining table.
Figure 3:
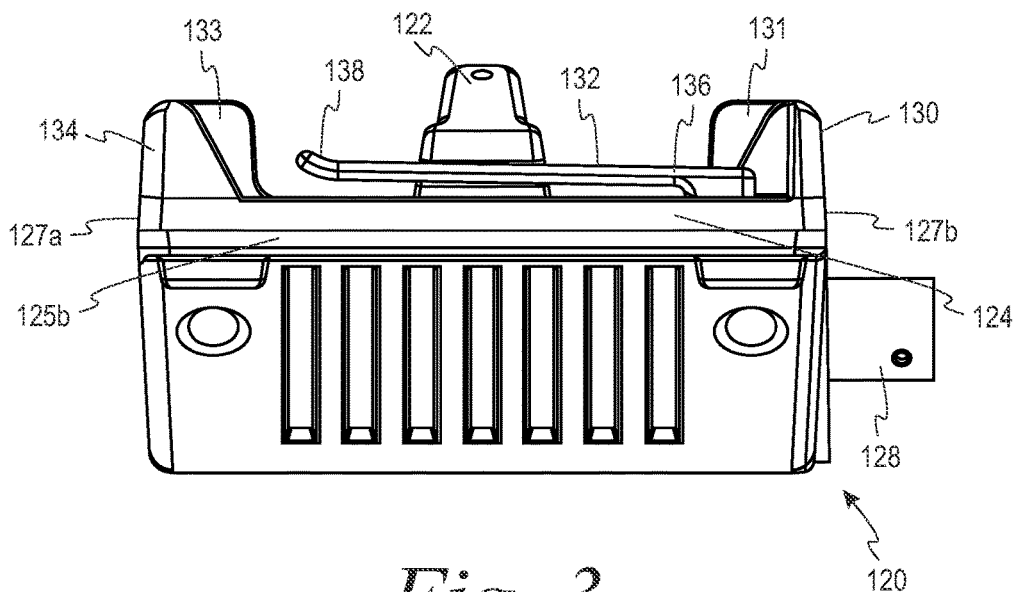
FIG. 3 is a front view of the retaining table of FIG. 2.

FIGS. 2-3 illustrate an exemplary first embodiment of a retaining table 120 for use with a fluid processing system. The table 120 includes a plate 124. It will be appreciated that this is an example in which the plate refers to an upper structural element of the table, wherein the plate 124 has a generally flat top surface and has opposed first and second ends 125a, 125b, and opposed first and second lateral edges 127a, 127b for supporting a disposable container or bag, such as the container 21 of FIG. 1. In this example, the table is configured for end-to-end oscillatory movement. The lateral edges are perpendicular to an axis of rotation through a drive shaft 128 or drive shaft coupling, which may be used to oscillate the retaining table 120, consistent with the axis of rotation 38 and drive shaft 28 of FIG. 1. As previously noted, alternative means of movement may be provided.

As shown in FIG. 2, the plate may be generally rectangular in shape, however, it is within the scope of the current disclosure for the plate to be of alternative shape, such as for example a square, an oval or a shape having a combination of straight and curved edges. In this example, the first end 125a may be curved, as depicted in FIG. 2. However, it is within the scope of the disclosure for the first end 125a to be straight like the second end 125b is depicted. Similarly, second end 125b and lateral edges 127a and 127b may be slightly curved, although they are straight in the example shown in FIG. 2.

The embodiment of FIGS. 2-3 optionally includes four retaining structures to keep a disposable container on the retaining table 120, which are disposed along the ends and lateral edges of the plate 124, respectively. For example, a first retaining structure 122 is connected to the plate 124 along the first end 125a. In this example, the first retaining structure 122 is configured as a clip. A second retaining structure 132 is connected to the plate 124 along the second end 125b. The second retaining structure 132 for securing the container to the table 120 is configured as a bar. The bar 132 has a first end connected to the plate 124 and a second end spaced above and parallel to or angled away from the plate 124. At least a central portion of the bar 132 is spaced above the plate 124. The bar 132 serves as a second retaining structure by permitting a portion of a container or tubing extending from a container to extend under the bar 132 and outward from the table 120.

The retaining table 120 optionally may include at least one retaining structure connected to the plate 124 along at least one of the first and second lateral edges 127a, 127b. The retaining structure may be, for example, a barrier extending upward from the plate, such as the barriers 130, 134 along respective lateral edges 127a, 127b. The clip 122, bar 132 and barriers 130, 134, or other optional retaining structures, may be connected to the plate by any suitable means relative to the particular structures, such as via mechanical fasteners, adhesive bonding, welding, integral forming or the like.

The retaining table 120 may be configured for movement and referred to as a dynamic table or as a table providing a plate having a dynamic surface. For example, the table 120 may have an axis of rotation that is perpendicular to the lateral edges 127a, 127b of the plate 124, and be configured to be connected to a drive shaft 128, consistent with the axis of rotation 38 and drive shaft 28 shown in FIG. 1. A portion of the motor drive shaft 128 (which may be a coupling) also is shown in FIG. 2 and may for example impart oscillation. It will be appreciated that the dynamic aspect may be provided by an alternative drive system, or by alternative motion, such as orbital or vibratory, which may be provided by suitable drive systems.

The plate 124 optionally may include a temperature adjusting element for cooling and/or heating the disposable container, or alternative apparatus such as for measurements or alternative manipulation of the fluid within the container. In this example, a temperature adjusting element 126 is configured as a plate fastened to and disposed on the top surface of the plate 124. It will be appreciated that the temperature adjusting element or other equipment may be connected to the plate via mechanical fasteners, adhesive bonding or the like, or may be integrally formed as part of the upper surface of the plate and/or table. In the example embodiments, the plate, table, and retaining structures may be at least partially formed of one or more metallic, plastic or alternative substantially rigid materials.

The retaining table 120 of this example includes the clip 122 along the first end 125a, as a first retaining structure for a disposable container. However, other structures may be used for this purpose, consistent with this disclosure, such as a post, a pivot-locking mechanism, a snap fit structure, a cam device, or other suitable structure. Additional details of the clip 122 and alternative first retaining structures in the form of clips will be discussed with respect to examples shown in FIGS. 4-8, followed by discussion of other first retaining structures, second retaining structures, and as additional retaining structures that may be use along the lateral edges.

The alternative clips of FIGS. 4-8 may be utilized in the first embodiment of FIGS. 2-3. Any of the different clips may be used as part of a retaining table assembly in place of clip 122 and with a retaining structure at the second end 125b and optionally with retaining structures, such as in the form of barriers along the lateral edges 127a, 127b of the plate 124. In each clip embodiment in FIGS. 4-8, a mobile (movable) jaw is pivotally secured to a base that is connected to the plate 124.

Each clip may have at least one protrusion on at least one of the mobile jaw and/or the base. In addition, the mating surface of the other of the at least one of the mobile jaw and base may have at least one recess sized to receive the at least one protrusion. Although in each embodiment different features are altered, such as the handle, and placement or shape of the protrusion, the features are interchangeable among the different clips and may be combined to provide additional embodiments consistent with the present disclosure, although not specifically shown. For example, a clip may include a compact or exposed handle and a protrusion and recess may be alternatively located on the mobile jaw and stationary base. The protrusions and recesses also may vary in number and shape. There may be a single or multiple protrusions and recesses. The protrusion(s) and recess(es) may be circular, pentagonal, trapezoidal, triangular, or any other suitable shape and complementary to each other. The material and texture of the protrusion, engageable surfaces of base and/or movable jaw also may be selected to improve gripping, such as by comprising a compliant material.

Figure 4:
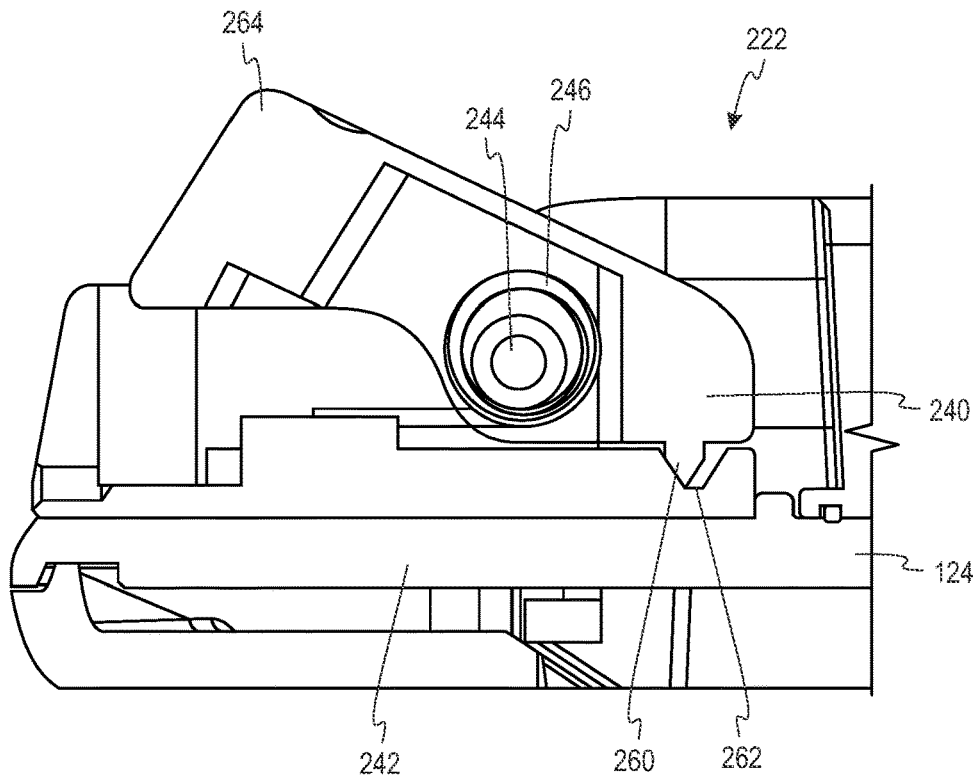
FIG. 4 is a schematic side view of a first embodiment of a clip area of a retaining table.

FIG. 4 illustrates a preferred first example clip 222, which is consistent with clip 122 but will be described in further detail. The clip 222 includes a mobile jaw 240 and a base 242, which is stationary and connected to plate 124. The base may be connected to the plate by any suitable means, such as via mechanical fasteners, adhesive bonding, welding, integral forming or the like. The mobile jaw 240 is pivotally connected to the base 242 by a pivot pin 244. The mobile jaw 240 also is biased to a closed position by a biasing element 246 in the form of a torsion spring, although it will be appreciated that a biasing element of an alternative configuration may be used. The mobile jaw 240 has a handle portion 264 that is compact and without any extending members. This handle configuration avoids any type of tangling between tubes extending from a disposable container and the clip 222. The handle portion 264 is pressed toward the base 242 to pivot the mobile jaw 240 to an open position for loading or unloading a container.

A protrusion 260 extends from the mobile jaw 240 and is received in a recess 262 of the stationary base 242 when the movable jaw 240 is in a closed position. The recess 262 is shaped and sized large enough to provide clearance to release the protrusion 260 when pivoting the mobile jaw 240 to an open position for removal of a bag or when moving a bag into position to be retained by the clip 222. In this example, the protrusion 260 and recess 262 may be at least partially pentagonal in shape and may include a triangular outside portion, or may be of other suitable shapes.

Figure 5:
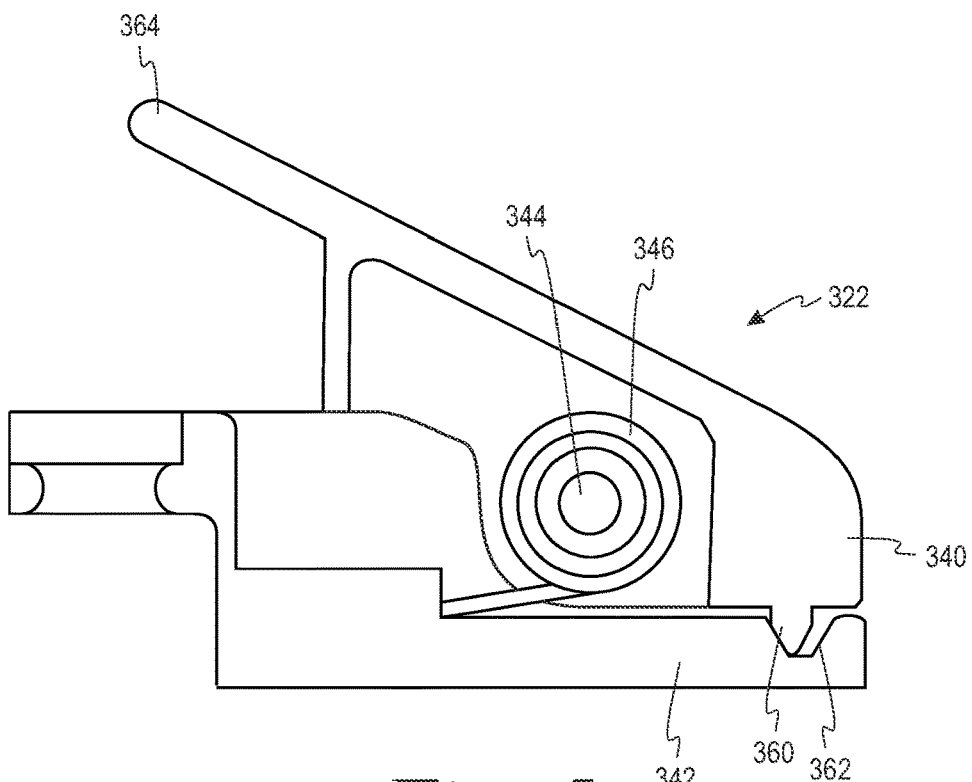
FIG. 5 is a schematic side view of a second embodiment of a clip for a retaining table.

FIG. 5 illustrates a second example of a first retaining structure for retaining a container, in the form of an alternative clip 322, which may be connected to a plate, consistent with one of the ways previously described. The clip 322 of FIG. 5 differs primarily from that of the clip 222 of FIG. 4 in that the clip 322 has a mobile jaw 340 that includes an exposed handle portion 364, which extends outward. The exposed handle portion 364 may be of any shape and size and may have a generally rectangular cross section, as shown in FIG. 5. Similarly to the previous example, the mobile jaw 340 is pivotally connected to a base 342 by a pivot pin 344. The mobile jaw 340 also is biased to a closed position by a biasing element 346, such as a torsion spring, although other biasing elements may be used.

A protrusion 360 extends from the mobile jaw 340 and is received in a recess 362 of the stationary base 342 when the mobile jaw 340 is in a closed position. The recess 362 is shaped and sized large enough to provide clearance to release the protrusion 360 when pivoting the mobile jaw 340 to an open position. The protrusion 360 and recess 362 may be at least partially pentagonal in shape and may include a triangular outside portion or other configuration. Optionally, the recess 362 may be configured to releasably secure the protrusion 360 when the mobile jaw 340 is in the closed position.

Figure 6:
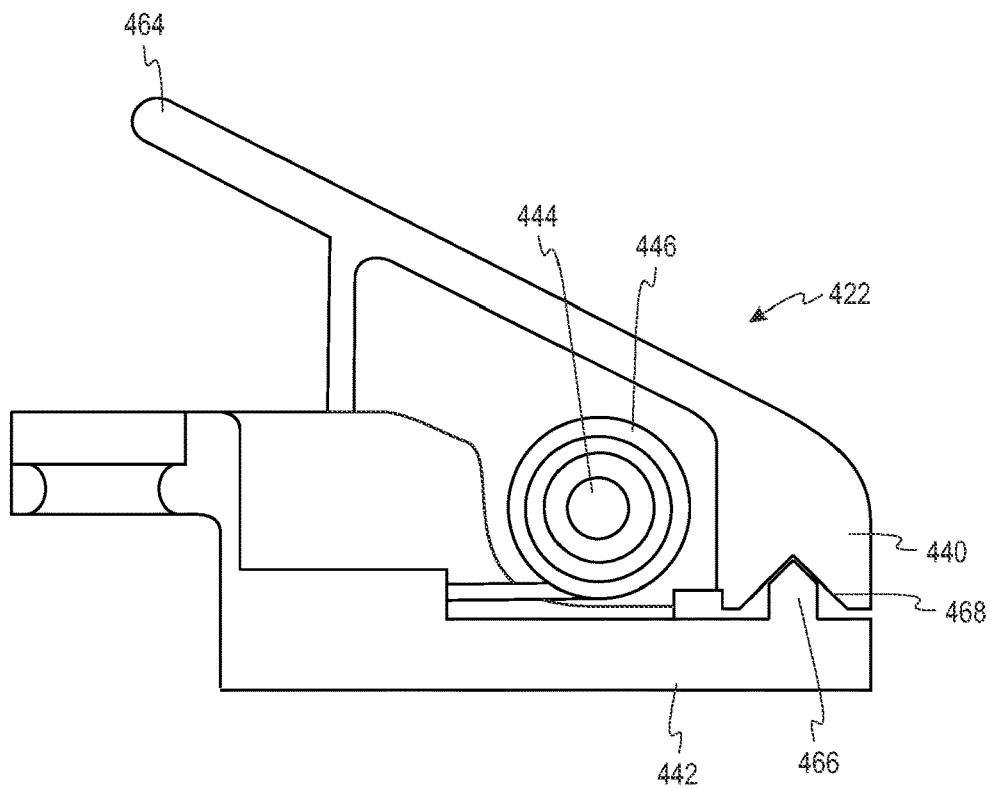
FIG. 6 is a schematic side view of a third embodiment of a clip for a retaining table.

FIG. 6 illustrates a third example of a first retaining structure for retaining a container, in the form of another alternative clip 422, which may be connected to a plate, consistent with one of the ways previously described. The clip 422 of FIG. 6 has a similar configuration to the clip 322 of FIG. 5 having an exposed handle portion 464 on a mobile jaw 440 that is pivotally connected to a base 442 by a pivot pin 444 and biased to a closed position by a biasing element 446. However, the clip 422 includes a different protrusion and complementary recess configuration. A protrusion 466 extends from a stationary base 442 of clip 422. A recess 468 is formed in the opposed surface of the mobile jaw 440. The recess 468 does not require as much space in this arrangement, wherein the protrusion 466 is configured as a tooth that readily fits within the recess 468 and has clearance when pivoting the mobile jaw to an open position. The protrusion 466 and recess 468 may be at least partially pentagonal in shape and may include a triangular outside portion or be of other suitable complementary shapes.

Figure 7:
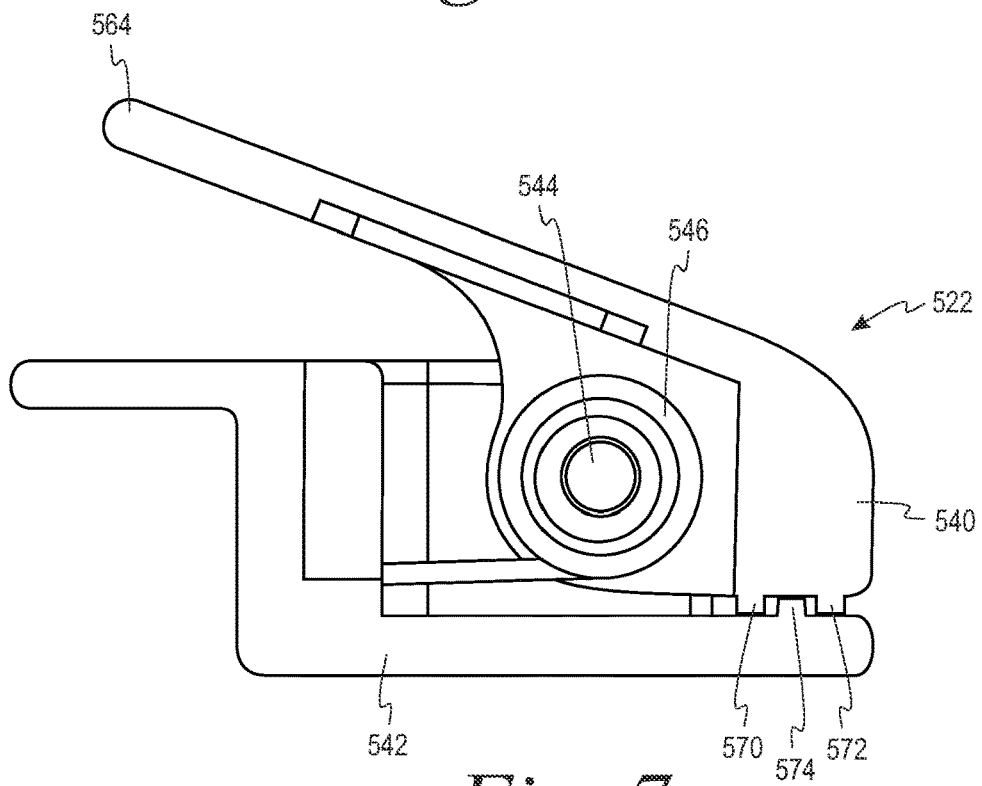
FIG. 7 is a schematic side view of a fourth embodiment of a clip for a retaining table.

FIG. 7 illustrates a fourth example of a first retaining structure for retaining a container, in the form of another alternative clip 522, which may be connected to a plate, consistent with one of the ways previously described. The clip 522 includes an exposed handle portion 564 on a mobile jaw 540 that is pivotally connected to a base 542 by a pivot pin 544 and biased to a closed position by a biasing element 546. However, the clip 522 includes a different protrusion and complementary recess configuration that optionally may be used on the clip 222 having a compact handle portion 264.

The clip 522 includes multiple protrusions 570, 572, and 574. Protrusions 570 and 572 extend from the mobile jaw 540 toward the base 542, and protrusion 574 extends from the stationary base 542 toward the mobile jaw 540. Alternatively, protrusions 570 and 572 may extend from the stationary base 542 and protrusion 574 may extend from the mobile jaw 540. In yet another alternate embodiment, protrusions 570, 572, and 574 may extend from the mobile jaw 540 only or from the stationary base 542 only.

As with other embodiments, whichever portion of the clip include a protrusion, the other or opposed portion may have complementary recess. It will be appreciated, however, that the portion of the clip without a protrusion alternatively may be flat, without a complementary recess. Also, while three protrusions are shown in the example of FIG. 7, two or more than three protrusions alternatively may be used. Preferably, the protrusions will be configured to alternate between extending from the mobile jaw and from the stationary base. The protrusions also may be on only one of the mobile jaw or base. The protrusions of the example shown in FIG. 7 are shown as having a generally rectangular configuration but may be pentagonal, circular, triangular or alternatively shaped.

Figure 8:
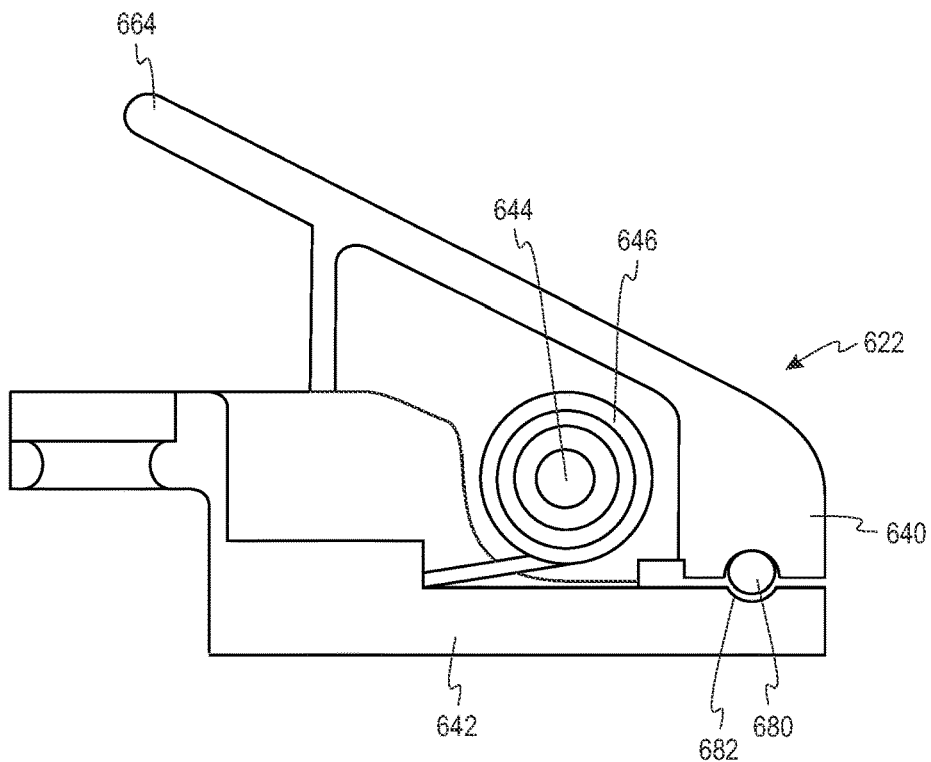
FIG. 8 is a schematic side view of a fifth embodiment of a clip for a retaining table.

FIG. 8 illustrates a fifth clip embodiment 622 as a first retaining structure. The clip 622 is similar to clip 322 of FIG. 5 but includes a circular shaped protrusion 680 extending from a mobile jaw 640, which is received by a complementary shaped recess 682 in a base 680. The base 680 may be connected to a plate in a stationary position, consistent with one of the ways previously described. The clip 622 includes an exposed handle portion 664 on the mobile jaw 640 that is pivotally connected to the base 642 by a pivot pin 644 and biased to a closed position by a biasing element 646. The circular shaped protrusion 680 may be constructed of a compliant material which enables the protrusion 680 to at least slightly deform and increase the contact area with a retained bag. As noted with respect to the previous example clips, the protrusion alternatively may be on the base, with the recess on the mobile jaw.

The clip mating faces (protrusion and recess) can be varied in additional ways not specifically shown. The mating faces of the clip may vary not only in shape, structure, and size, but also in material. In certain embodiments, including those with a protrusion or recess, the mating faces for features may be composed of the same material as the rest of the clip, including plastics or metals. Additionally, the mating faces may be composed of a compliant material, such as rubber or the like. In such embodiments, due to the more compliant material, the recess and/or protrusion may not be needed. For instance, the material may be compliant enough that the protrusion interacts directly with the base and does not require a recess. Both mating faces may be constructed of a compliant material, which may remove the need for the protrusion and recess. The clip also may be modified by changing to a different biasing member structure, by changing the distance between the pivot axis and the end of the handle portion and/or the distance between the pivot axis and the gripping end of the mobile jaw.

As noted previously, the plate 124 optionally may include a second retaining structure along the second end 125b, which may be a bar 132. FIGS. 2-3 more clearly show the bar 132, having one end angled away from the plate 124. For example, the bar may have first and second ends 136, 138, respectively. The first end 136 may be secured to the plate 124 near the lateral edge 127b and the bar 132 may be configured to be spaced from and extend laterally across at least a portion of the plate 124, with the second end 138 extending further away from the plate 124 at an angle, near the lateral edge 127a, but not secured to the plate. In one embodiment, the bar may be adjusted to the size of the bag with a hinge or other adjustable mechanism at the first end, where it is secured to the plate. A bar having a second end angled away from the plate is preferred for retaining a container directly or via retention of tubing extending from the container along the second end of the plate. However, it will be appreciated that other second retaining structures may be used.

When used in combination with a clip at the first end of the plate, it is important that the second retaining structure that holds the second end of the disposable container does not fix the container to the plate. The second end typically will need to accommodate a portion of the disposable container having at least one tube extending therefrom. The particular structure of one or more tubes that extend from a disposable container may vary significantly and the angled end of the bar may accommodate tubes of various sizes and constructions to slide into the space between the bar 32 and the plate. The bar 132 also may serve as a barrier and tend to hold down a container or block it from sliding, while allowing a tube to pass under the bar.

The retaining table 120 of FIGS. 2-3 also optionally includes at least one barrier as a retaining structure along each lateral edge 127a, 127b and which extends upward from the plate 124. FIG. 2 illustrates barriers 130, 134, along the respective opposed lateral edges. The example side barriers 130, 134 are raised walls extending upward from the plate 124. An inner surface on a section of the barrier wall may extend upward at an angle, while an outer surface of the barrier wall generally may extend upward vertically or also at a slight angle. The angled inner surfaces of the side barriers 130, 134 serve as an additional feature to help center the disposable container when placing it on the plate 124, as well as to hold the container in place and/or continue to bias the container toward a centered position disposed over the temperature adjusting element 126.

The barriers 130, 134 may include a thicker portion 131, 133 near the clip 122 and first end 125a of the plate 124. The thicker portions 131, 133 may act as a barrier at the first end 125a of the table 120. These portions may absorb some of the force from a container that is subjected to rotation during oscillatory mixing and help control such force to avoid inadvertent opening of the clip 122. The barriers 130, 134 may be constructed as solid walls integrally formed with the plate or may be separate structures connected to the plate by conventional means of fastening. The side barriers may present solid surfaces, may have openings extending therethrough, or be configured as a bar having at least a portion spaced from and above the plate.

To assist in positioning and approximately centering disposable containers or bags of various lengths and widths over a plate and over a temperature adjusting element, measurement or other manipulation equipment or other apparatus for which location of the container is important, a first retaining structure for fixing the container to the plate at the first end may be adjustable. In this particular example, the adjustment is configured to be in a direction along the longer axis of the retaining table and perpendicular to a rotational axis. FIGS. 9-12 illustrate a second embodiment of a retaining table of the present disclosure with such an adjustable clip configuration. The first retaining structure is adjustably connected to two barriers along the respective first and second lateral edges of the plate. This embodiment includes a clamp system connected to the first retaining structure and releasably lockable along the two barriers to permit adjustment for preferable centering of different length disposable containers along the dynamic retaining table.

In reference to FIGS. 9-12, the example retaining table 720 is similar to retaining table 120 in that it includes a plate 724 having a generally flat upper surface and an optional temperature adjusting element 726. While any of the first retaining structures disclosed herein may be utilized in a length adjustable configuration, this example includes a clip 722 as a first retaining structure along a first end 725a. A bar 732 provides an optional second retaining structure along a second end 725b. However, at least one further retaining structure in the form of side barriers 750, 752 along lateral edges 727a, 727b of the plate 724 may be of a different configuration than in the previous embodiment, which permits the location of the clip 722 to be adjustable relative to the first end 725a.

The side barriers 750, 752 are fixed to the plate 724 and include wall portions 754, 756, which are fixedly connected to the plate 724, such as by mechanical fasteners, bonding or by being integrally formed therewith. The side barriers 750, 752 also include fixed adjustment portions 758, 760, which include rod-shaped portions parallel to and spaced from the top surface of the plate 724 having notches 758a, 760a that are open outward, although it will be appreciated that the orientation of the notches will be based on the configuration of the releasable locking mechanism associated therewith. The adjustment portions 758, 760 have a first end fixedly connected to the plate 724 and a second end fixedly connected to and extending from one of the fixed wall portions 754, 756, respectively, with the fixed connections being by conventional means, such as those previously described.

The clip 722 has a base 742 and a mobile jaw 740, which is pivotally connected to the base 742 via a pivot pin 730 and is biased to a closed position by a biasing element (not shown). The base 742 of the clip 722, or an alternative first retaining structure, is fixedly connected to a yoke 744. The yoke 744 is constructed as a thin, flat bracket that is parallel to and may slide along or be spaced from the top generally flat surface of the plate 724. Also, fixedly connected to the yoke 744 is a clamp system 734. The clamp system 734 includes clamp devices 746, 748 that are slidably and lockingly connected to the respective side barriers 750, 752, at the adjustment portions of 758, 760, along the first and second lateral edges 127a, 127b of the plate 124. The clamp system 734 permits the position of the yoke 744, and therefore, the clip 722 to be adjusted relative to the first end 725a of the plate 724.

Each clamp device 746, 748 includes a base and a latch that engages a respective barrier. The clamp devices 746, 748 slidably receive the respective adjustment portions 758, 760 and are moveable along the respective lateral edges 727a, 727b of the plate 724. The latch of the clamp devices 746, 748 may be in the form of a release mechanism. The release mechanism may be a button, cam latch, thumb screw, or other suitable release mechanism, including the example mechanisms illustrated in FIGS. 12-14.

Figure 9:
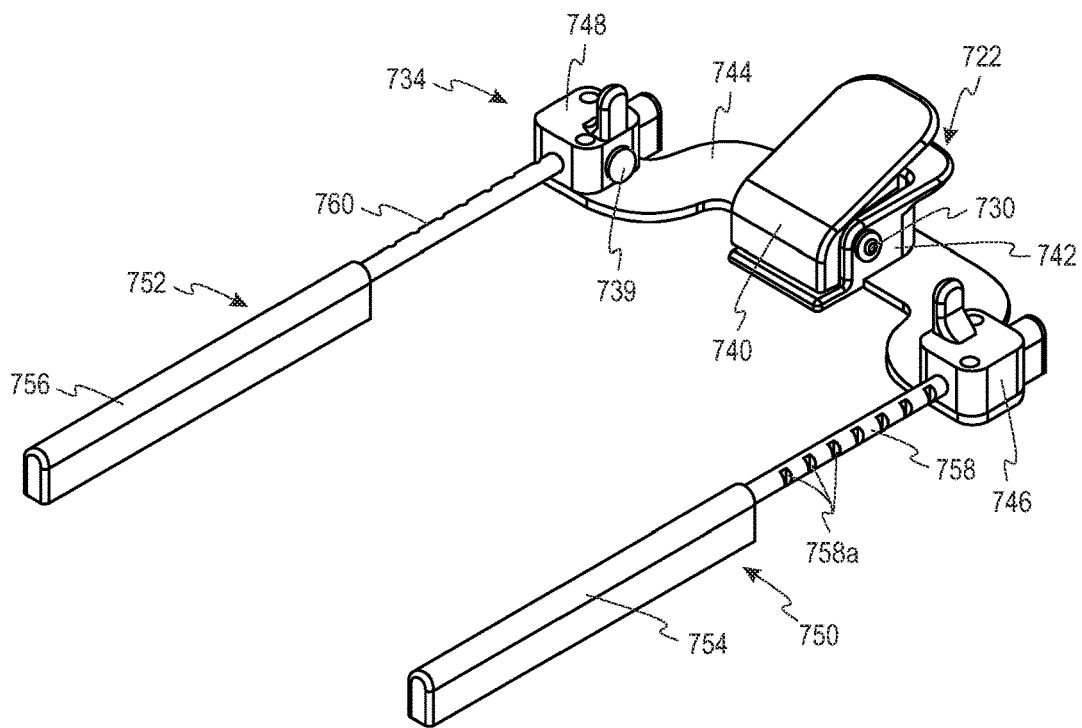
FIG. 9 is a perspective view of a first embodiment of a clip and clamp system, which are part of a second embodiment of a retaining table of FIG. 10.
Figure 10:
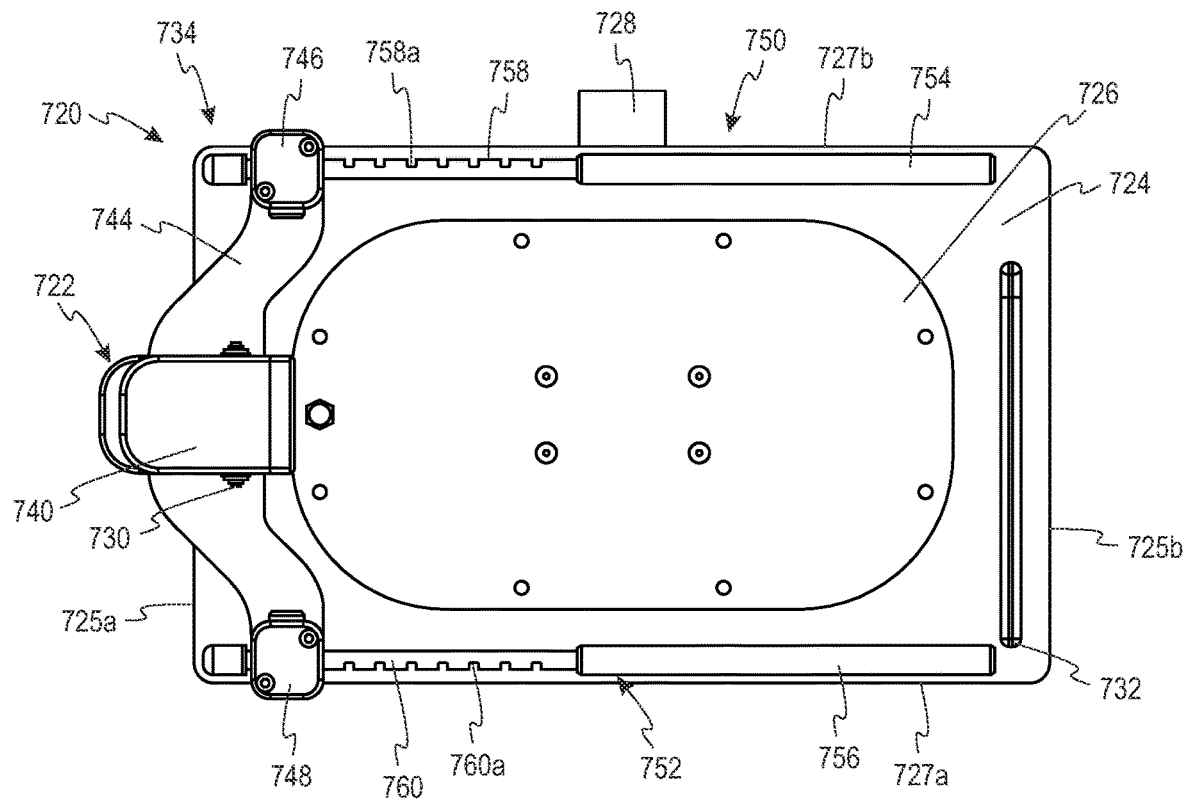
FIG. 10 is a top view of the second embodiment of a retaining table.
Figure 11:
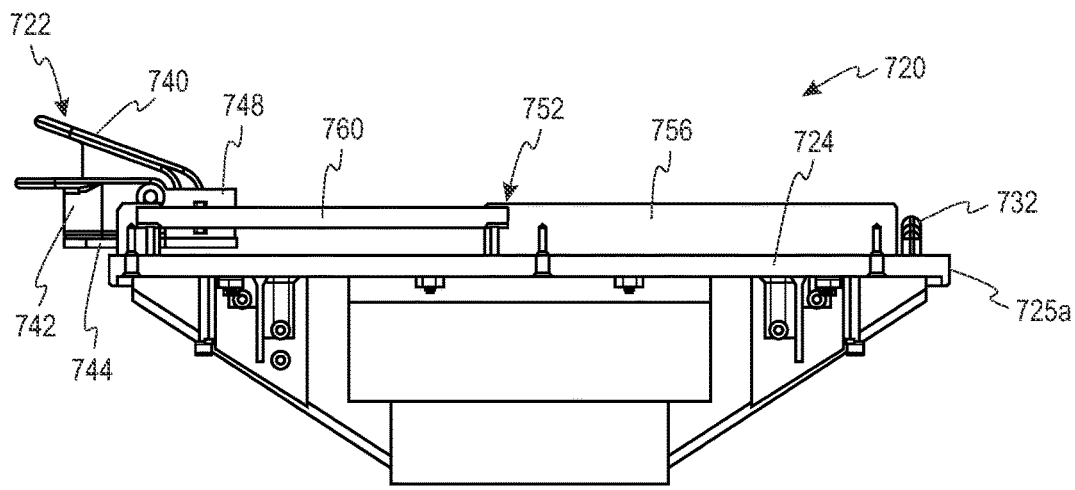
FIG. 11 is a partial cross-sectional side view of the retaining table of FIG. 10, with the near side barrier in partial cross section.
Figure 15:
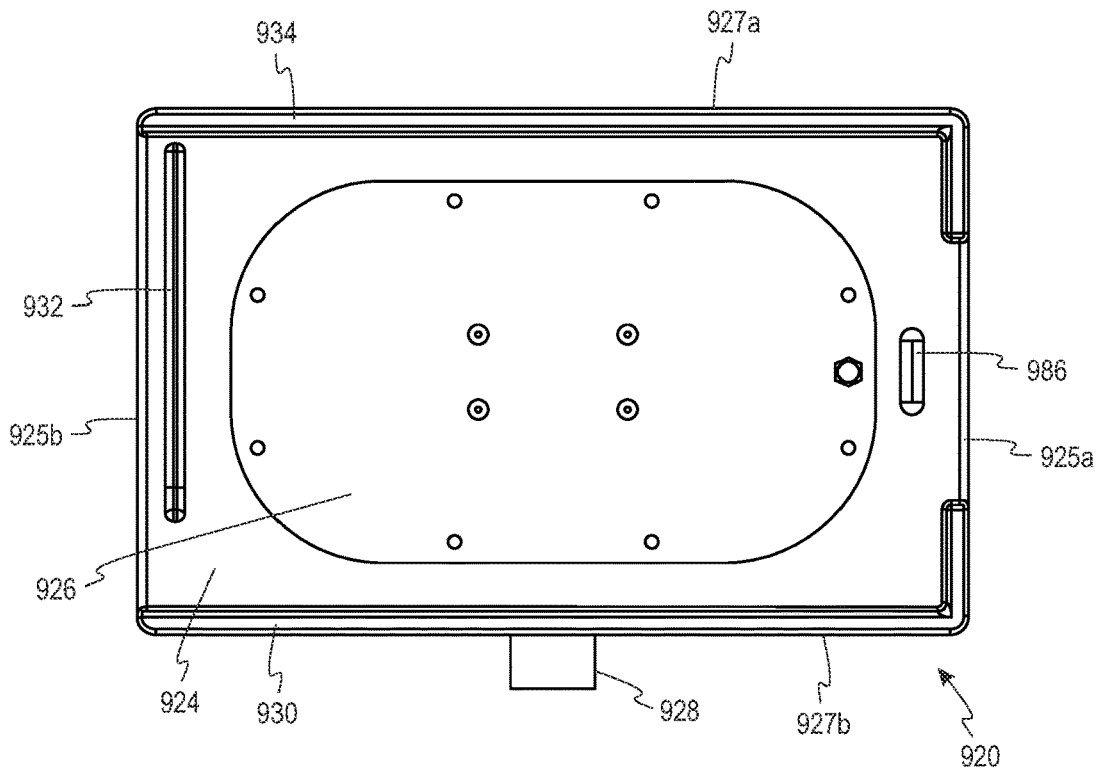
FIG. 15 is a top view of a third embodiment of a retaining table.
Figure 16:
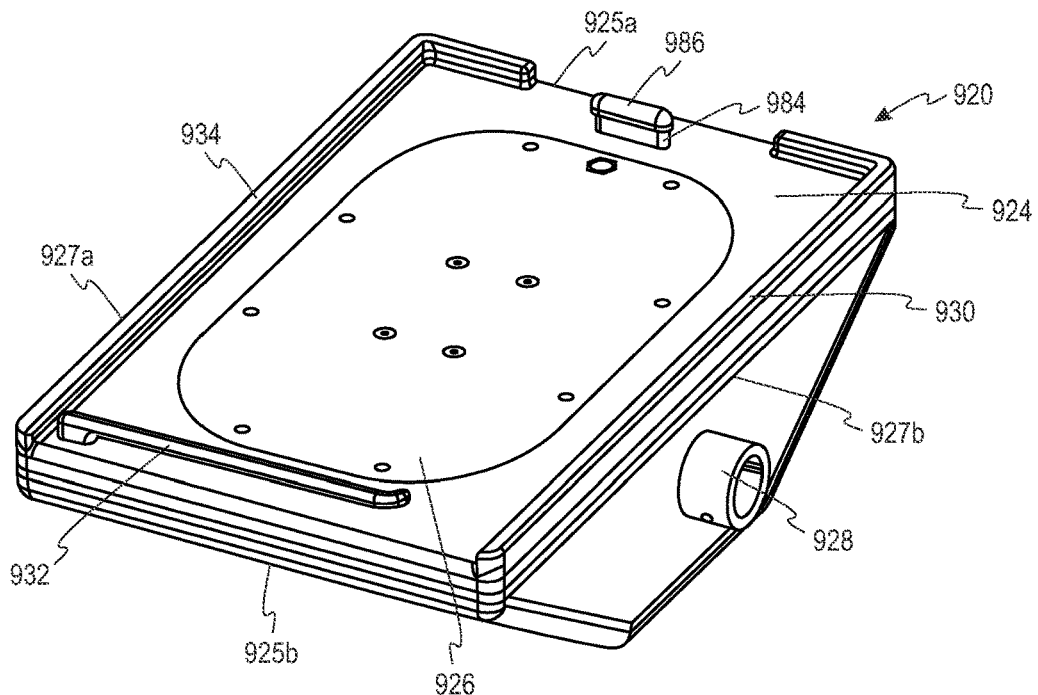
FIG. 16 is an upper perspective view of the retaining table of FIG. 15.
Figure 17:
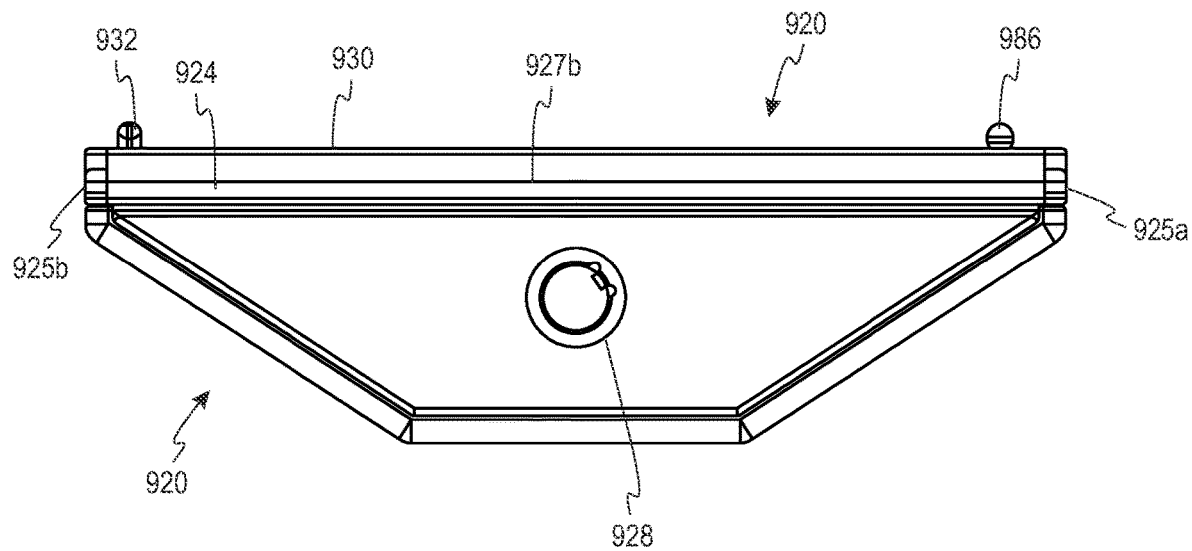
FIG. 17 is a side view of the retaining table of FIG. 15.
Figure 18:
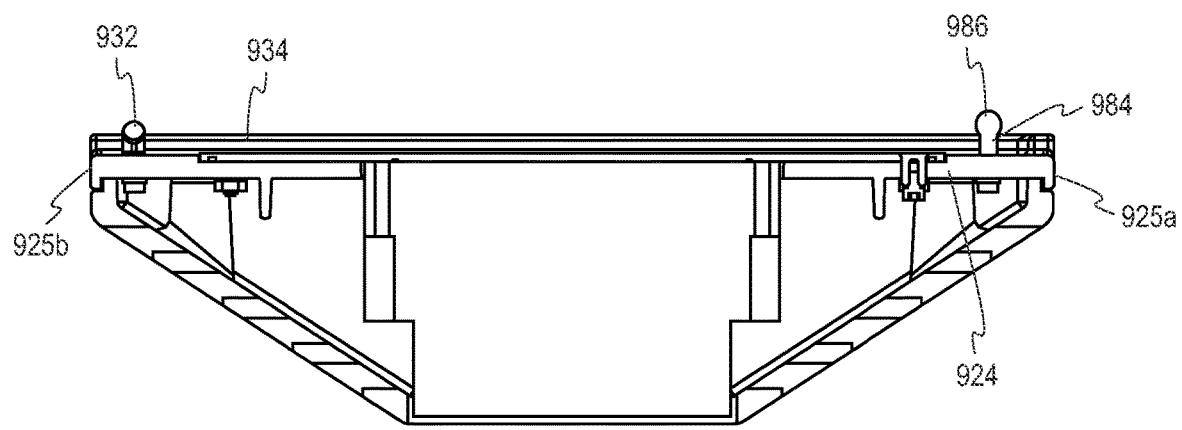
FIG. 18 is a side cross-sectional view of the retaining table of FIG. 15.

FIG. 12 shows a portion of the example clamp device 746, which may be utilized in the clamp system 734 of the example retaining table 720 of FIGS. 9-11. The clamping device 746 includes a latch 737, which is biased into a locking position in one of the notches 758a of the adjustment portion 758, such as by a spring 735. A release button 739 may be pressed to force the latch 737 out of the notch 758a while compressing the spring 735. It will be appreciated that the clamp device 748 may have a similar structure to that of 746. Upon release of the clamp devices 746, 748, the yoke 744 may be moved along the plate 724 to adjust the position of the clip 722. When the release buttons are no longer pressed, the latches will be biased into a locking position in selected notches 758a, 760a of the respective adjustment portions 758, 760.

FIGS. 13-14 illustrate a second embodiment of a clamp system 834 that may be substituted for the clamp system 734 of FIGS. 9-11. The clamp system 834 includes clamp devices 846, 848 and is shown connected to a yoke 844, which is similar to yoke 744. Each of the clamp devices 846, 848 slidably and lockingly receives an adjustment portion, such as the adjustment portion 858, having downward opening notches 858a, as may be seen in FIG. 14. The clamp devices 846, 848 include a lever 829a, 829b, respectively.

As will be appreciated with respect to the clamp device 846 in FIG. 14, lifting an end of the lever 829a will cause the oblong shaped body of the lever 829a to pivot about a pin 830 and thereby to force a latch 831 downward. The latch 831 is biased toward an upward position, such as by springs 833. In the upward position, a lower portion 835 of the latch 831 is received in a downward opening notch 858a of the adjustment portion 858, locking the clamp device 846 and preventing movement along the adjustment portion 858. Lifting the lever 829a compresses the springs 833, thereby removing the lower portion 835 of the latch 831 from the notch 858a in the adjustment portion 858. The lever 829a provides a convenient grip location and may remain in an unlocked position while moving the clamp device 846. It will be appreciated that the latch 831 is biased upward toward a locked position by the springs 833, so the lever 829a may be closed without engaging a notch 858a, but the latch 831 will automatically engage a notch 858a when the clamp device 846 is moved along the adjustment portion 858, such as may occur if the retaining table starts oscillating.

It will be appreciated that the side barriers 750, 752 may be alternatively configured relative to those shown in FIGS. 9-14. For example, the barrier portions may be larger or smaller with less space between the adjustment portions and the plate. The notches also may be alternatively configured such as by having different shapes or a different number of notches, depending on the configuration of the clamp devices. Alternatively, the adjustment portions of the side barriers may be constructed of a compliant material, such as rubber, the latches may engage and deform the adjustment portions to an extent whereby notches may not be required to attain a locked position.

As noted previously, it will be appreciated that the plate used on a dynamic retaining table may be a separate component connected to the table or may be integrally formed as a top portion of the table, and may be alternatively equipped with different retaining means for holding disposable containers or bags along a first end, whether fixedly attached to or positionally adjustable relative to the plate. FIGS. 15-18 illustrate a third example embodiment of a retaining table 920 without a clip of the prior example embodiments along a first end 925a of a plate 924. The first end 925a of the plate 924 may include a first retaining structure having an upstanding portion 984 configured as a post or elongated projection having an enlarged head 986. It will be appreciated that the upstanding portion 984 may be of any suitable length. The enlarged head 986 may be of any length and/or shape that may aid with retaining a disposable container or bag. For example, the enlarged head may be mushroom shaped. This may be particularly advantageous when the disposable containers or bags include an aperture or slot near one end. The retaining table 920 may be oscillated via the coupling or drive shaft 928. As noted previously with respect to the examples illustrated herein, the table may be driven by an alternative oscillatory drive, or may be subject to other dynamic movement, such as orbital or vibratory by use of a further alternative drive system.

The table 920 also includes a second retaining structure in the form of a bar 932 having a portion spaced from the top surface of the plate 924 and disposed along a second end 925b of the plate 924. The retaining table 920 also optionally may include at least one barrier along lateral edges 927a, 927b. The example table 920 is shown with barriers 934, 930, along the respective lateral edges 927a, 927b of the plate 924. The barriers may be similarly or differently shaped relative to the example barriers of the previous embodiments.

FIGS. 19-22 illustrate two related alternative embodiments for retaining a disposable container on a retaining table used with a processing system. Each figure includes a plate, which would be connected to a dynamic table, as in the previous examples. Also, as in the previous examples, each plate has a generally flat top surface with opposed first and second ends and opposed first and second lateral edges for supporting a disposable container. Although not shown in FIGS. 19-22, the plates also may include at least one side barrier of a type as previously described, such as including fixed walls, adjustable bars or the like. However, as with the previous examples, it is not required to have a barrier along either lateral edge.

Figure 19:
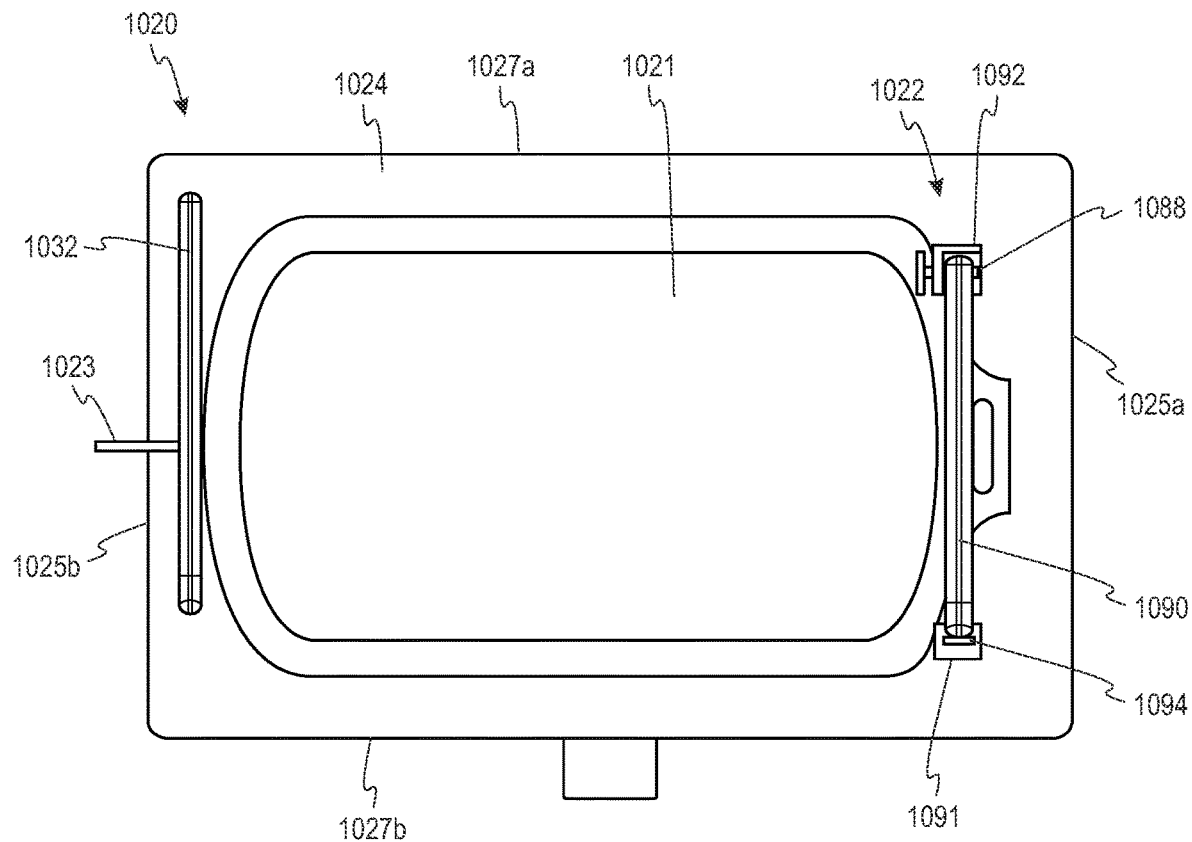
FIG. 19 is a top view of a fourth embodiment of a retaining table.
Figure 20:
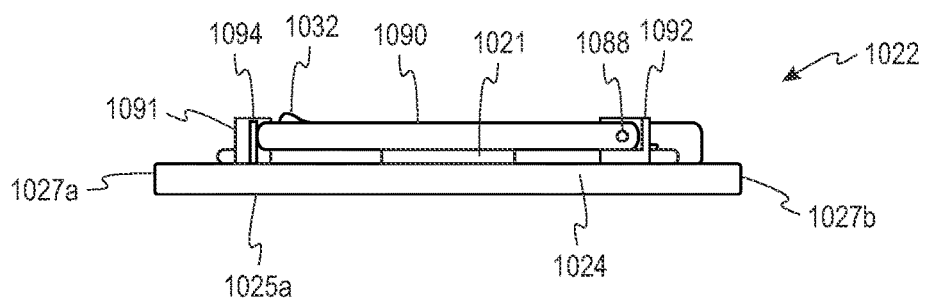
FIG. 20 is an end view from the first end of the plate of the retaining table of FIG. 19.

A fourth embodiment of a retaining table 1020 is illustrated in FIGS. 19-20. A releasable locking system 1022 of the example in FIGS. 19-20 is provided as a first retaining structure disposed along a first end 1025a of a plate 1024. The locking system 1022 includes a first stationary block 1091 and second stationary block 1092, which are connected to the plate 1024, near respective opposed lateral edges 1027b, 1027a, respectively. A mobile (movable) bar 1090 is pivotally secured to the first stationary block 1091, such as by a hinge 1094 or other pivoting attachment means at the first end of the mobile bar 1090. On the second end near lateral edge 1027a, the mobile bar 1090 is releasably connected to the plate 1024 via the second stationary block 1092.

A pin 1088 releasably engages and locks the mobile bar 1090 in a closed position. The pin 1088 is movably connected to the stationary block 1092 that is connected to the plate 1024. The bar 1090 may be released to pivot upward to an open position by pulling the pin 1088 in a direction away from the mobile bar 1090. The pin 1088 may be perpendicular to the mobile bar 1090 and engage the mobile bar 1090 in a way so as to block its pivotal movement upward, such as by engaging a notch or aperture in the mobile bar 1090, or in the second stationary block 1092 at a location above the mobile bar 1090. Once locked in place, the locking system 1022 secures a disposable container, such as container 1021, against the generally flat top surface of the plate 1024. The pin may be a pull pin and may include a retaining ring, or biasing member. Alternatively, the pin may be a threaded pin, ball detent pin or be of other suitable releasable structure. It will be appreciated that the disposable container 1021 may include tubing 1023 and the second end 1025b of the plate 1024 may utilize a second retaining structure in the form of a bar 1032 spaced above the top surface of the plate 1024, similarly to previous embodiments. The second end of the container and/or the tubing 1023 may extend beneath the bar 1032, thereby contributing to retaining the container 1021. Moreover, use of a mobile bar 1090 at the first end 1025a and bar 1032 at the second end 1025b may advantageously permit convenient routing of tubing extending from either end of the disposable container 1021.

Figure 21:
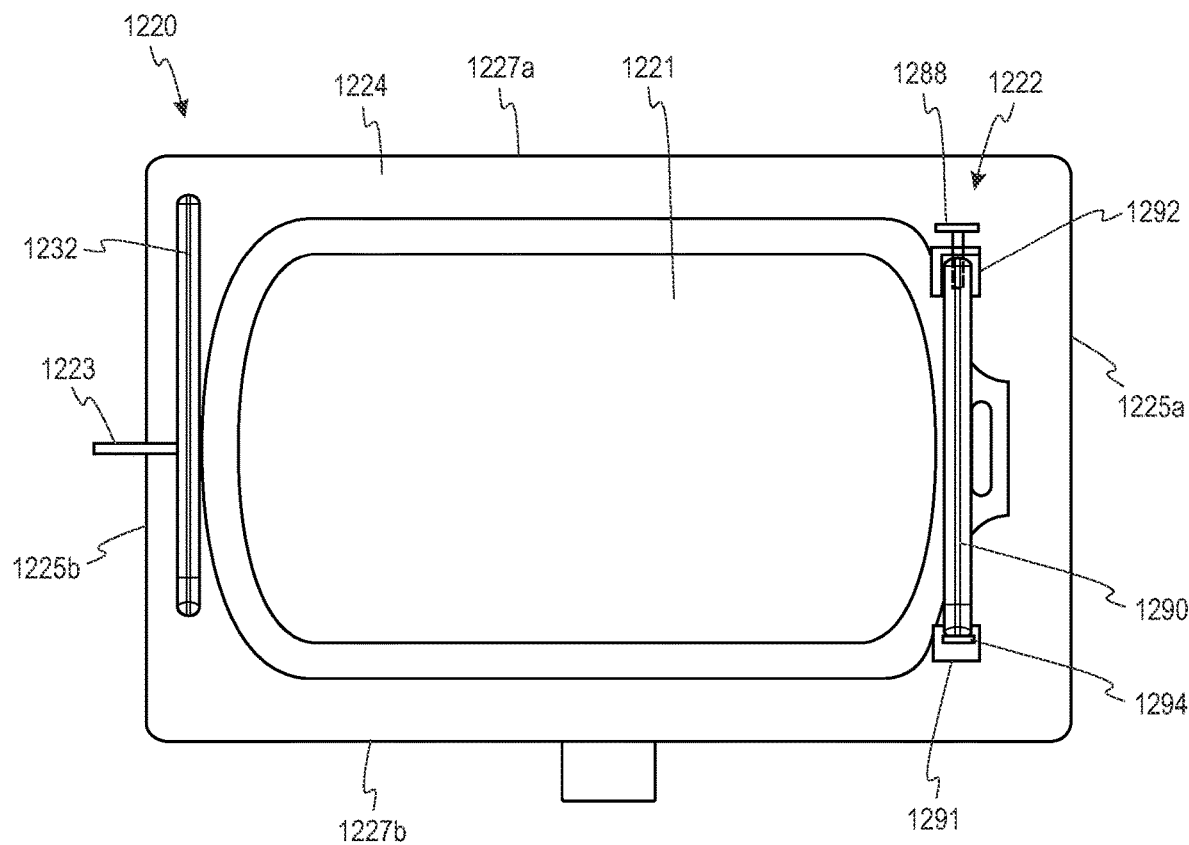
FIG. 21 is a top view of a fifth embodiment of a retaining table.
Figure 22:
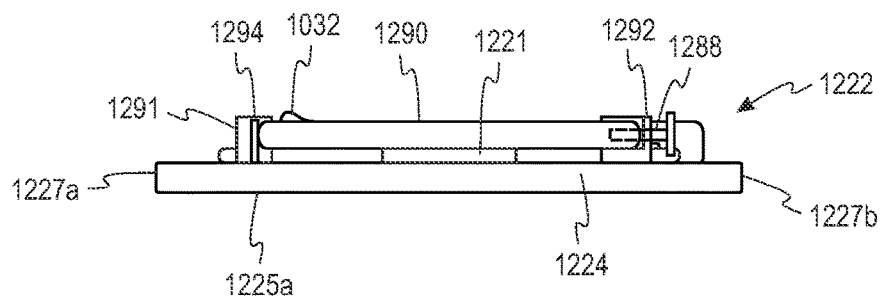
FIG. 22 is an end view from the first end of the plate of the retaining table of FIG. 21.

FIGS. 21-22 include a fifth embodiment of a retaining table 1220 somewhat similar to that of FIGS. 19-20. A first retaining structure is provided by a locking system 1222 at a first end 1225a of a plate 1224. However, in FIGS. 21-22, a pin 1288 is arranged parallel to a mobile bar 1290. With the configuration of FIGS. 21-22, the pin 1288 engages and is received by a recess 1293 in a second end of mobile bar 1290, instead of engaging the mobile bar in a perpendicular configuration. On the second end near lateral edge 1227a, the mobile bar 1090 releasably connects to the second stationary block 1292.

Thus, the locking system 1222 includes a first stationary block 1291 and second stationary block 1292, which are connected to the plate 1224, near respective opposed lateral edges 1227b, 1227a, respectively. A mobile (movable) bar 1290 is pivotally secured to the first stationary block 1291, such as by a hinge 1294 or other pivoting attachment means at the first end of the mobile bar 1290.

A pin 1288 releasably engages and locks the second end of the mobile bar 1290. The bar 1290 may be released by pulling the pin 1288 in a direction away from the mobile bar 1290. The pin 1288 may be parallel to the mobile bar 1290 and engage the mobile bar 1290 by being received in a recess 1293 in the second end of the mobile bar 1290. Once locked in place, the locking system 1222 secures a disposable container, such as a container 1221. The pin may be slidably received in the second stationary block 1292, or constructed consistent with the previously described alternative pin constructions. As in the previous examples, it will be appreciated that the disposable container 1221 may include tubing 1223 and the second end 1225b of the plate 1224 may utilize a second retaining structure in the form of a bar 1232 spaced above the top surface of the plate 1224. Use of a mobile bar 1290 at the first end 1225a and bar 1232 at the second end 1225b may permit tubing to be conveniently accessed and routed from either end of the disposable container 1221.

Depending on the configuration of the mobile bar and the pin in both of the fourth and fifth embodiments, the mobile bar may have notches, holes, and/or a recess for the pin to engage when locking the mobile bar after pivoting it downward to a closed position to retain a disposable container.

Figure 23:
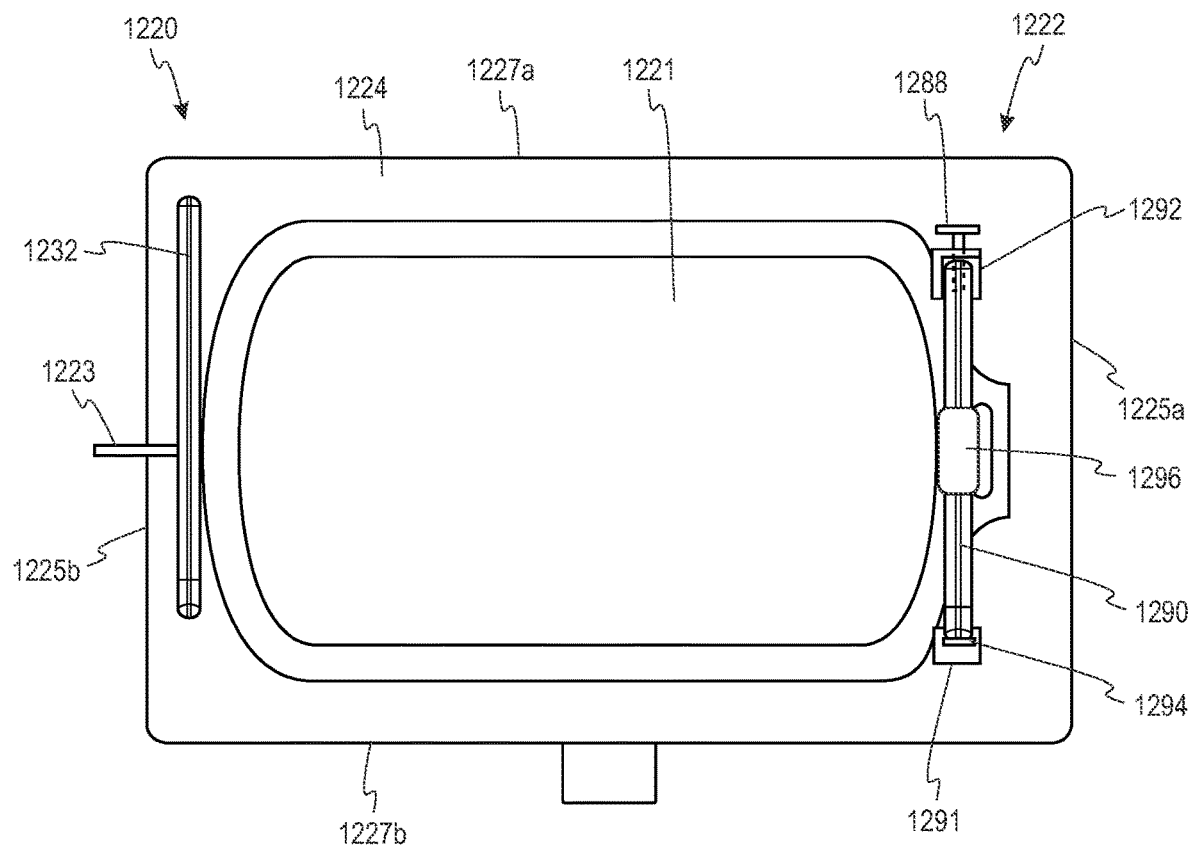
FIG. 23 is a top view of a modification to the retaining table of FIG. 21 including a cam on the first retaining structure.
Figure 24:
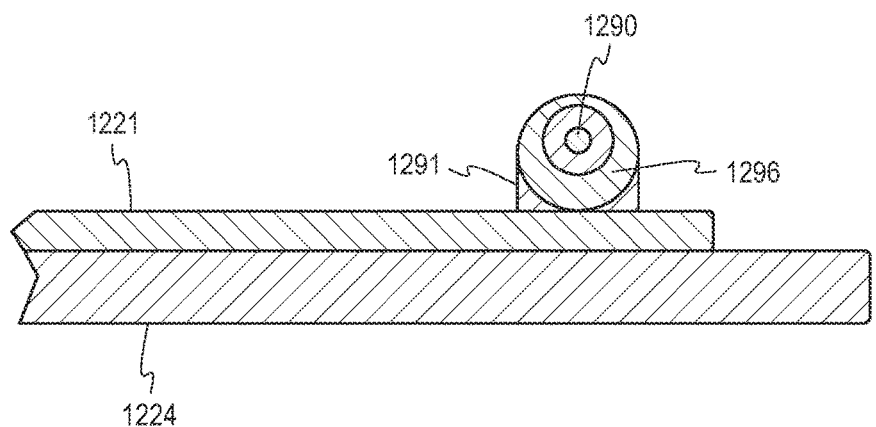
FIG. 24 is a side cross-sectional view including the cam on the first retaining structure of the retaining table of FIG. 23.

FIGS. 23-24 illustrate a modification to the fifth example embodiment of a retaining table 1220 shown in FIGS. 21-22. The modification includes a cam 1296 disposed on the bar 1290 and is configured to engage a container 1221. The cam 1296 may assist in stabilizing and gripping the container 1221. The cam 1296 may be rotatably adjustable relative to the bar. Thus, the cam 1296 may be connected to the bar 1290 about the longitudinal axis of the bar and rotated to a position to apply greater or lesser holding force against the plate 1224. The cam may be a variety of shapes including, but not limited to, circular/spherical, rectangular/cube or generally cam shaped, and may be configured to be located in one position or movable along the mobile bar 1290. The cam also may be constructed of various materials, including potentially of a compliant material to assist in gripping a container. It will be appreciated that a further modification may include having the first retaining structure configured as a rotatable bar, with the cam fixed rotationally relative to the bar, such that the position of the cam relative to the table is adjusted by rotation of the bar. Additionally, the cam may be located on a first retaining structure configured as a fixed bar, such that the cam may be rotated about the bar to permit loading of a container and then engaging the container to retain the container on the plate.

Figure 25:
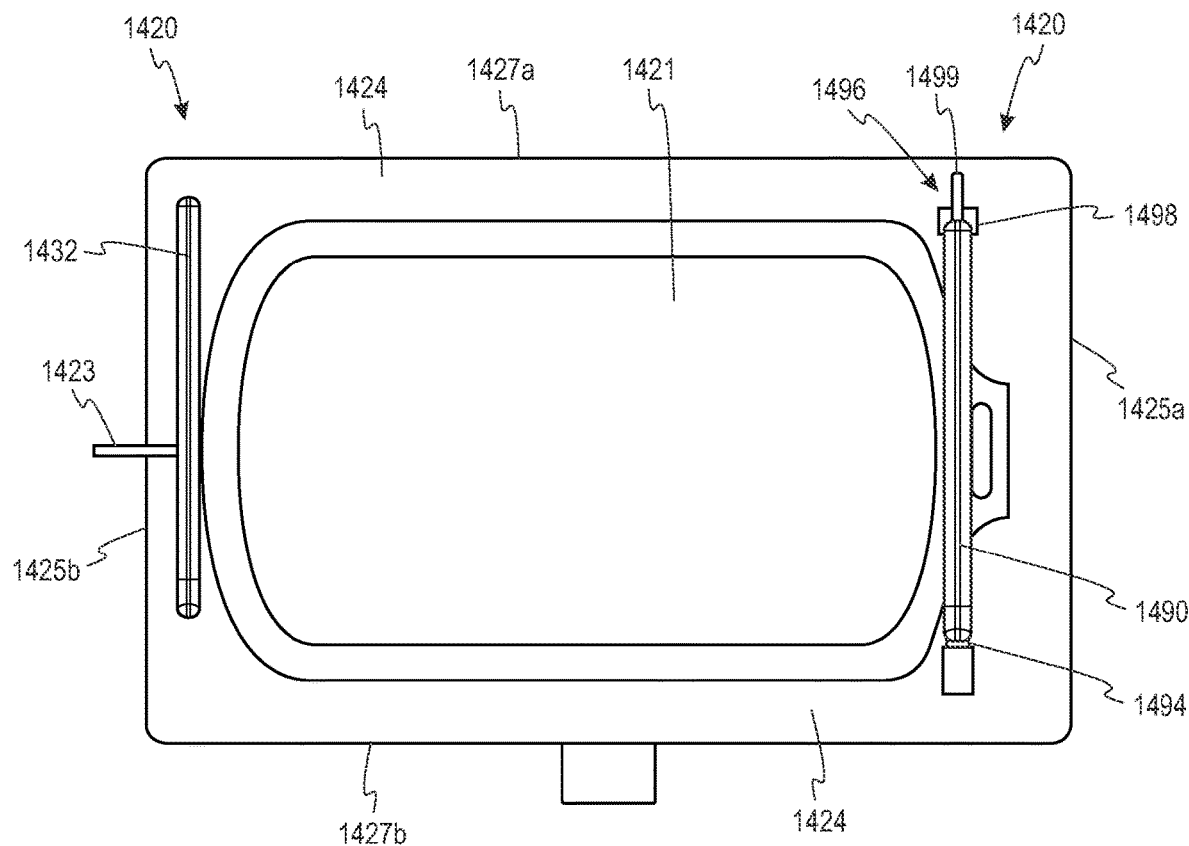
FIG. 25 is a top view of a sixth embodiment of a retaining table.
Figure 26:
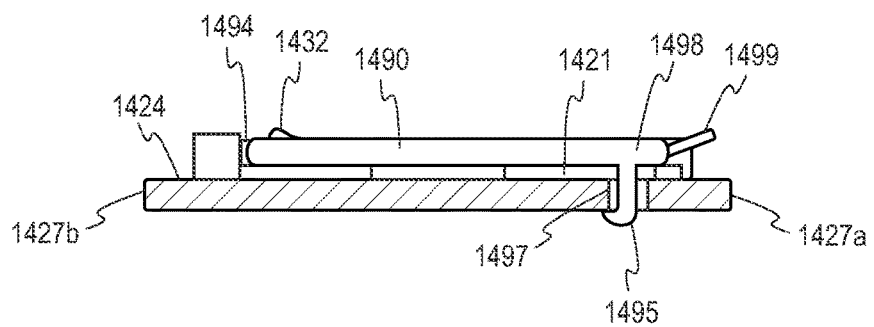
FIG. 26 is an end partial cross-sectional view from the first end of the plate of the retaining table of FIG. 25.

FIGS. 25-26 illustrate a sixth embodiment of a retaining table 1420. Table 1420 includes a plate 1424 having a generally flat top surface with opposed first and second ends 1425a, 1425b and opposed first and second lateral edges 1427a, 1427b for supporting a disposable container 1421. The retaining table 1420 also includes a first retaining structure configured to be a locking system 1496 along a first end 1425a of the plate 1424 comprising a mobile (movable) bar 1490 pivotally connected to the plate 1424 at a first end by a hinge 1494 and having a locking mechanism at a second end of the bar 1490 near lateral edge 1427a. The locking mechanism includes a latch 1498. The latch 1498 includes at least one protrusion 1495 at a second end of the mobile bar 1490 and an aperture 1437 through the plate 1420 configured to releasably receive the at least one protrusion 1495. Alternatively, the latch may include an aperture and the plate may have an upward extending protrusion that engages the latch when extending through the aperture. The latch 1498 also may include a handle 1499 for convenient grasping and actuation of the latch 1498. The locking system 1496 retains the container 1421 at the first end 1425a of the plate 1424. The table 1420 also may include a second retaining structure, such as the bar 1432, which may be similar to the bar at the second end in the previous examples, as well as additional side barriers, as previously discussed.

Figure 27:
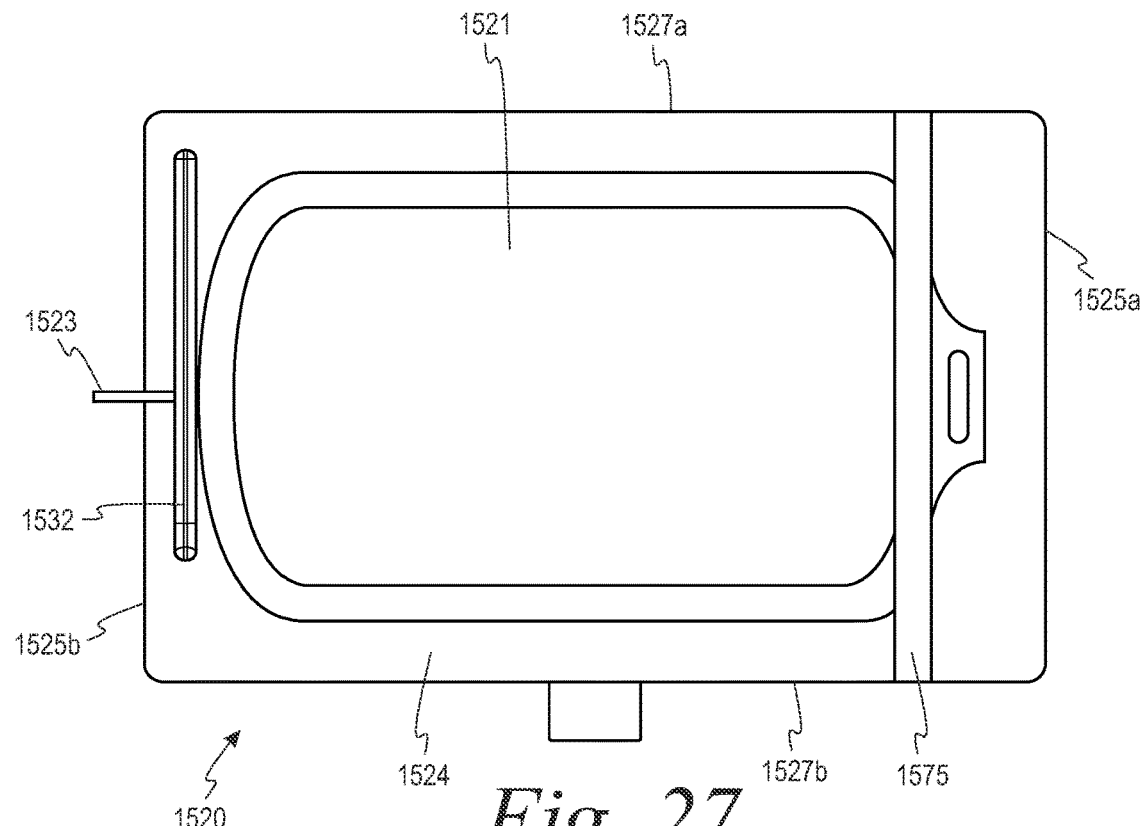
FIG. 27 is a top view of a seventh embodiment of a retaining table.

FIG. 27 illustrates a seventh embodiment of a retaining table 1520. The table 1520 has a plate 1524 having a generally flat top surface with opposed first and second ends 1525a, 1525b and opposed first and second lateral edges 1527a, 1527b for supporting a disposable container 1521. The retaining table 1520 includes a first retaining structure including a band 1575 along a first end 1525a of the plate 1524 extending from the first lateral edge 1527a to the second lateral edge 1527b. A second retaining structure is provided along the width of the second end 1525b of the plate 1524 by a bar 1532. This is similar to previous examples, such that the bar 1532 is connected to the plate 1524 at a first end and spaced above the plate 1524 along its length. The table 1520 optionally also may include retaining structures along the lateral edges 1527a, 1527b, such as the side barriers previously discussed in earlier examples.

Figure 28:
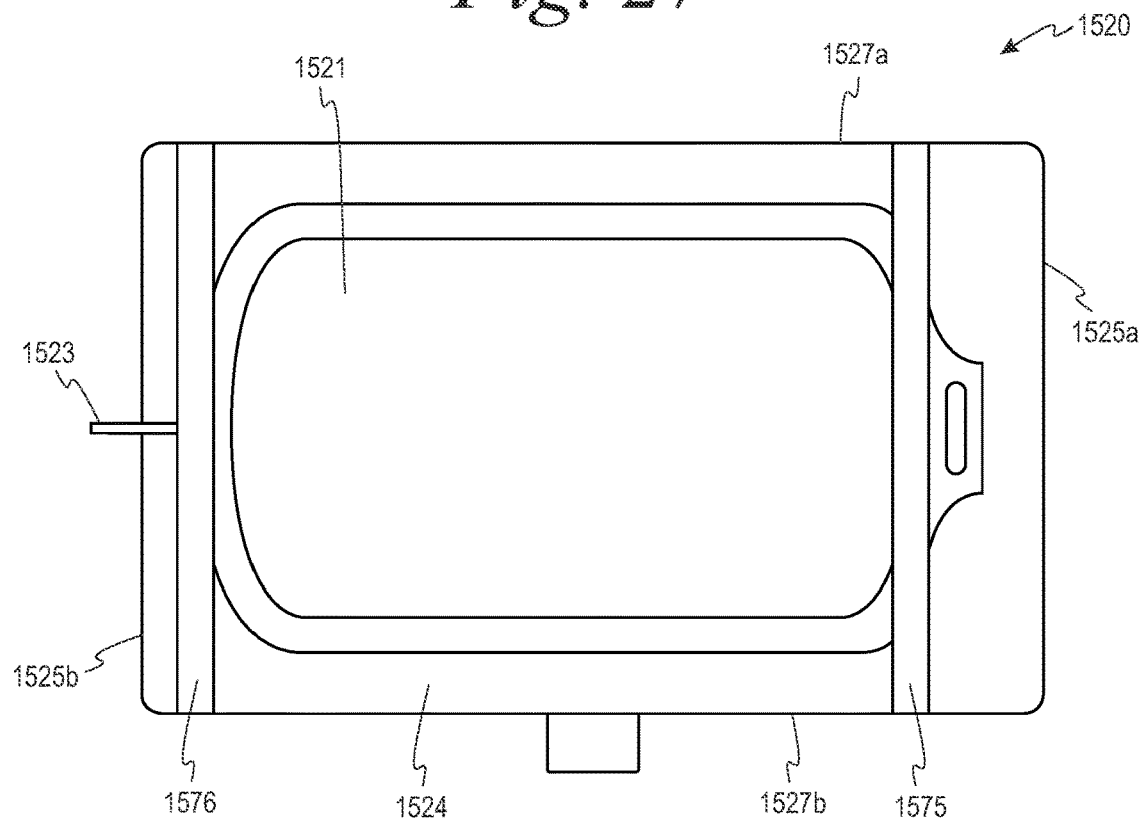
FIG. 28 is a top view of a modification to a second retaining structure of the retaining table of FIG. 27.

FIG. 28 illustrates a modification to the seventh embodiment of FIG. 27. In addition to the first band 1575, the retaining table 1520 optionally also may include a second retaining structure including a second band 1576 along the second end 1525b of the plate 1524 extending from the first lateral edge 1527a to the second lateral edge 1527b. This alternative retaining table embodiment also may include retraining structures along the opposed lateral edges, such as the previously discussed side barriers. In addition, the band 1576 at the second end 1525b may be used in combination with any of the other first retaining structures disclosed herein, whether configured for fixed or adjustable connection to the table.

Figure 29:
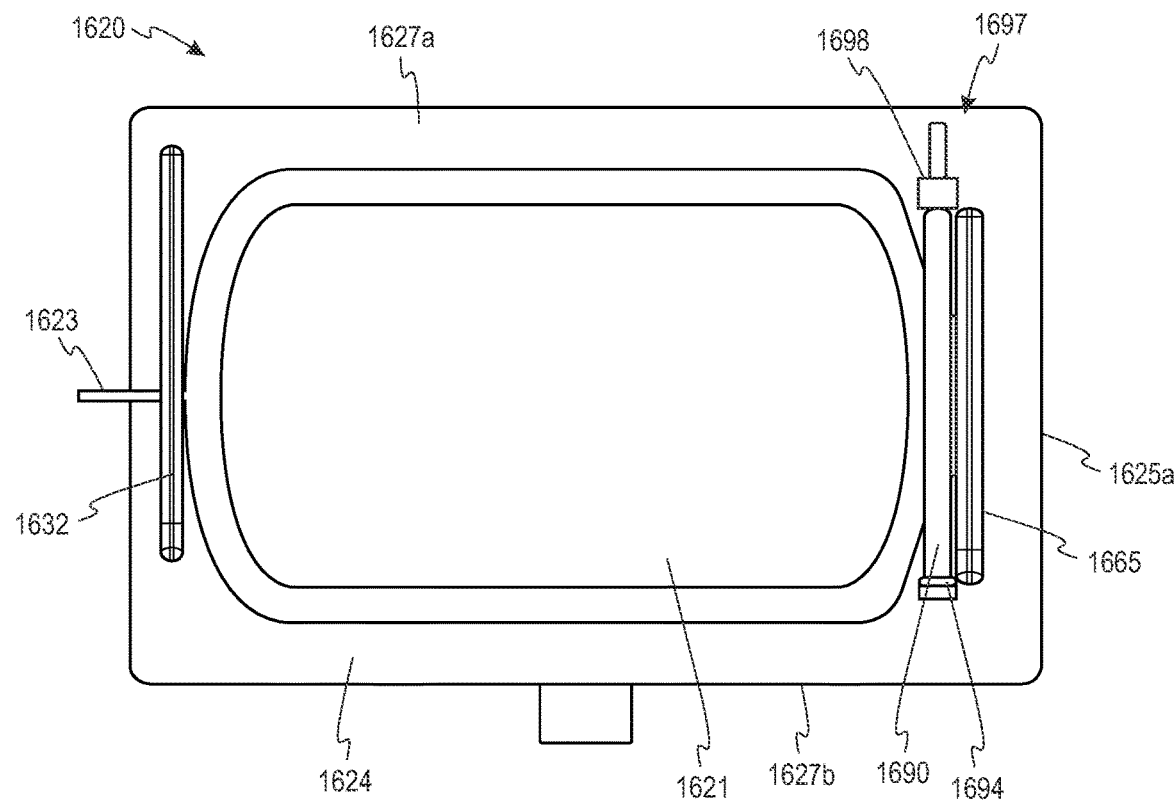
FIG. 29 is a top view of an eighth embodiment of a retaining table.
Figure 30:
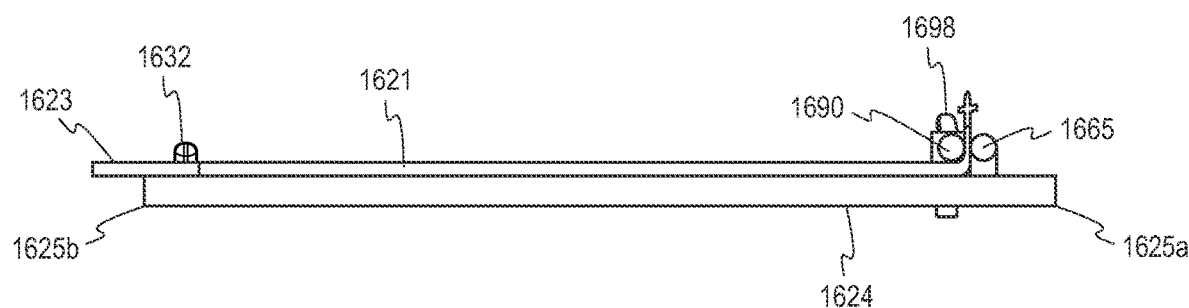
FIG. 30 is a schematic partial cross-sectional side view of the retaining table of FIG. 29.
Figure 31:
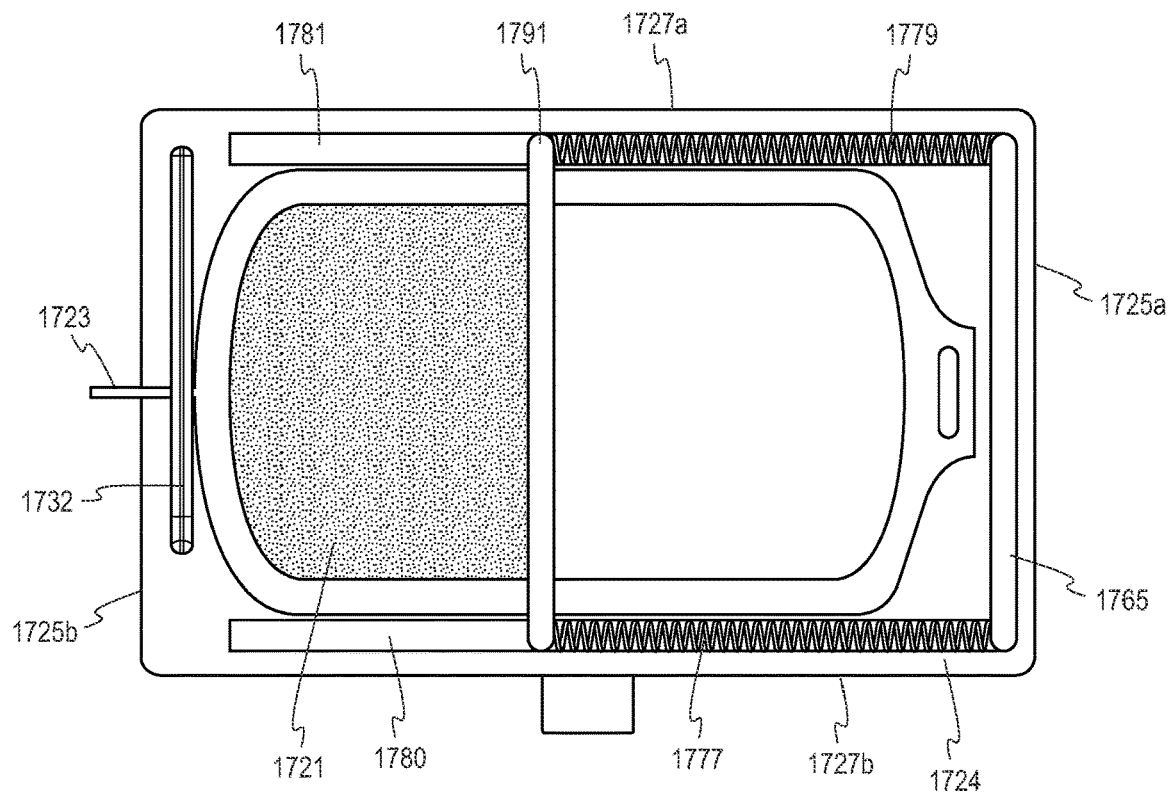
FIG. 31 is a top view of a ninth embodiment of a retaining table.

FIGS. 29-31 illustrate eighth and ninth example embodiments of retaining tables. The tables include a roller as part of the retaining structures. FIGS. 29-30 illustrate an eighth embodiment of a retaining table 1620 including a plate 1624 having a generally flat top surface with opposed first and second ends 1625a, 1625b and opposed first and second lateral edges 1627a, 1627b for supporting a disposable container 1621. The table 1620 further includes a first retaining structure including a stationary bar 1665 and a roller 1690 along the first end 1625a of the plate 1624. The roller 1690 is spaced apart from the stationary bar 1665. The roller 1690 also is pivotally connected to the plate at a first end, such as via a hinge 1694, releasably connected to the plate 1624 at a second end via a locking system 1697.

The locking system 1697 may include a releasable latch 1698. The latch may include at least one protrusion extending from a holder at the end of the roller 1690 and an aperture on the plate 1624 sized to receive the protrusion, or a protrusion extending from the plate 1624 and sized to be received by an aperture in a holder at the end of the roller 1690. Other latching means may be utilized. The roller 1690 is used to capture a first end of the container 1621. Thus, with the latch 1698 unlocked and the roller 1690 pivoted upward to an open position, the first end of a container 1621 that is disposed on the plate 1624 may be extended over the stationary bar 1665. With the upper end of the container 1621 extending over the bar 1665 along the first end 1625a of the plate 1624, the roller 1690 then may be pivoted about its first end to have the second end move downward to engage and squeeze the upper end of the bag between the roller 1690 and the bar 1665 and to engage the latch 1698. As noted with previous examples, the upper end of the bag may have one or more tubings extending from it, which may extend from the upper end being held by the bar 1665 and the roller 1690. A second retaining structure is provided at the second end 1625b of the plate 1624 in the form of a bar 1632, which is similar to previously described examples, and permits a tubing 1623 to extend therefrom. Additional retaining structures may be provided along the lateral edges.

FIG. 31 illustrates the ninth embodiment of a retaining table 1720, which also includes a first retaining structure having a stationary bar 1765 along a first end 1725a of a plate 1724 and a second retaining structure including a bar 1732 along a second end 1725b of the plate 1724. The table 1720 also may include further retaining structures in the form of side barriers, as previously discussed with other embodiments.

The retaining table 1720 in FIG. 31 includes a roller 1791 connected to the first end 1725a of the plate 1724 by springs 1777, 1779. For example, the springs are shown being connected to the stationary bar 1765, but it will be appreciated that the springs may be connected directly to the plate or to other intermediate structures, such as posts or the like. The springs are connected to roller holders that slide relative to the opposed guides 1780, 1781 along the lateral edges 1727a, 1727b of the plate 1724. The springs are configured to bias the roller 1791 toward the second end 1725b of the plate 1724. This may assist during filling and/or drainage of the container to tend to keep the fluid toward the second end 1725b of the table 1720. As fluid fills the container 1721 and the container 1721 expands in a direction away from the top surface of the plate 1724, the fluid will tend to push the roller toward the first end 1725a of the plate 1725. In a similar manner, as fluid is removed from the container 1724, the roller will be biased back toward the second end 1725b of the plate 1724. Thus, the roller 1791 is configured to move up and down along the plate 1724, toward and away from the second end 1725b. This may help to avoid retaining air in the container, to keep the fluid located toward one end of the container and to reduce forces that may otherwise be amplified by sloshing during oscillation of a partially filled container.

Figure 32:
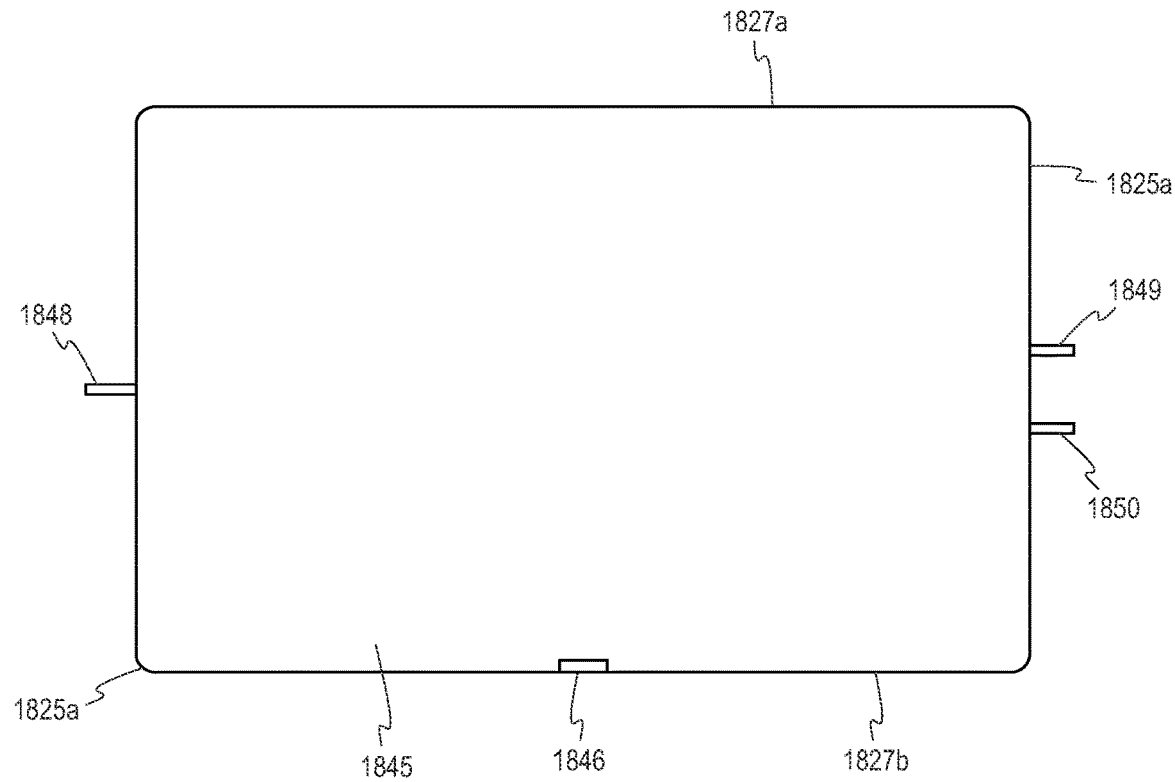
FIG. 32 is a top view of a tenth embodiment of a retaining table having a door in a closed position.
Figure 33:
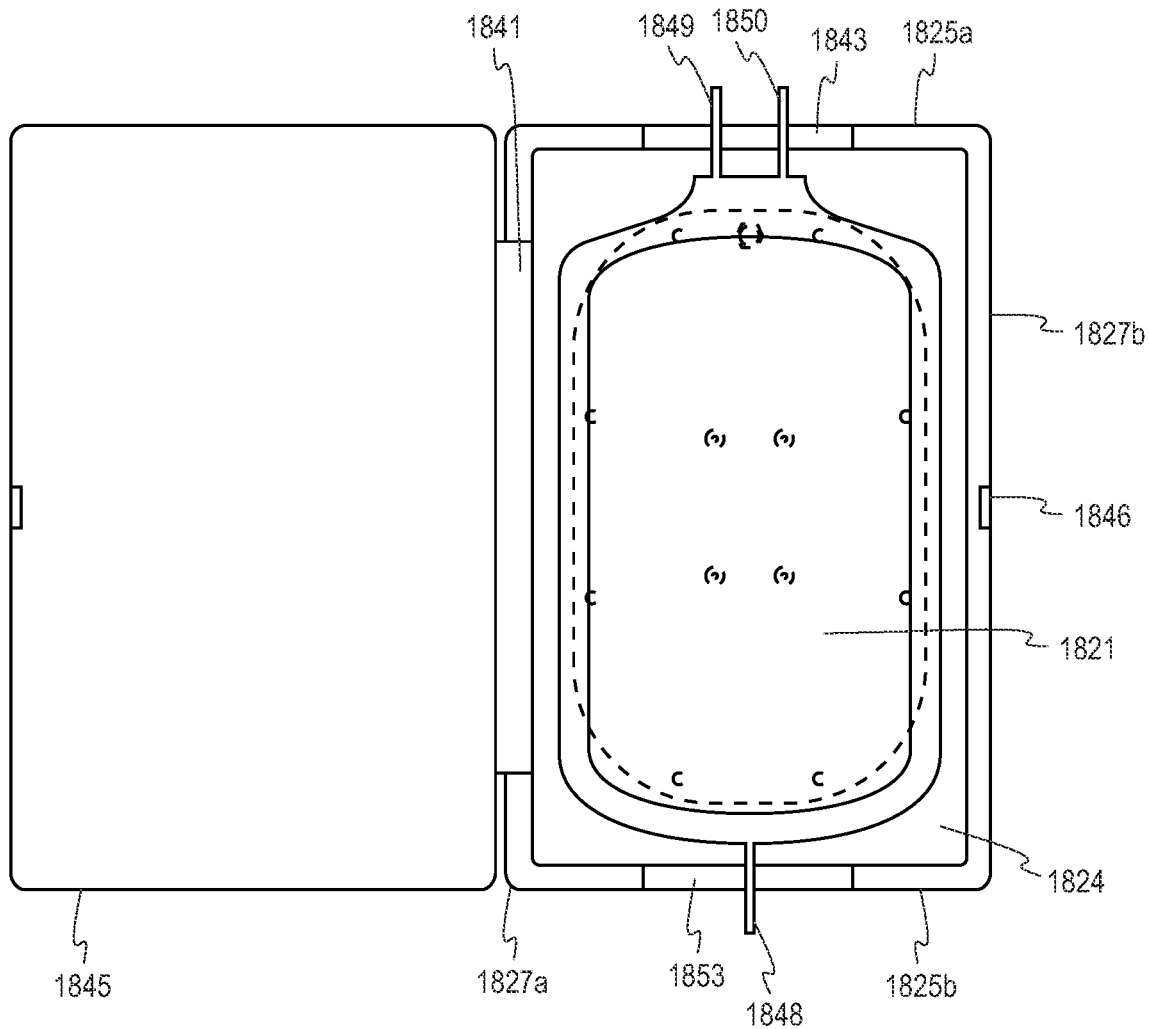
FIG. 33 is a top view of the retaining table of FIG. 32 with the door in an open position.
Figure 34:
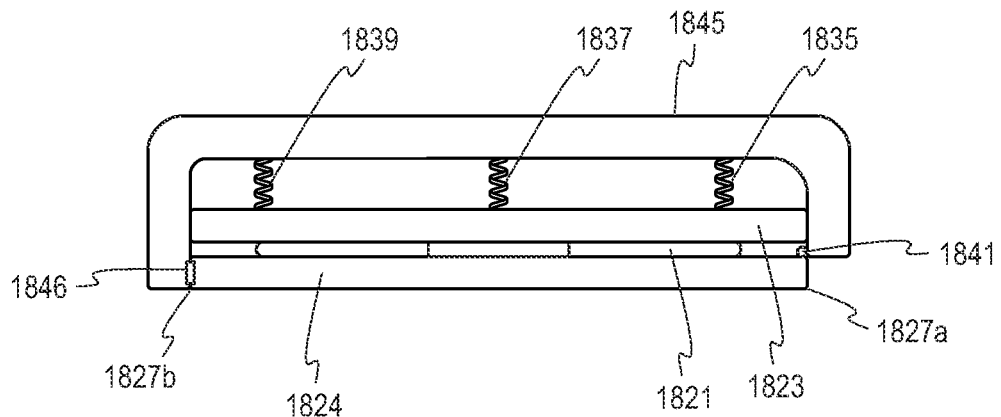
FIG. 34 is a schematic end view from the first end of the plate of the retaining table of FIG. 32.

FIGS. 32-34 illustrate a tenth embodiment of a retaining table 1820 for use with a fluid processing system. FIG. 32 shows the table in a closed position and FIG. 33 shows the table in an open position. FIG. 34 shows a cross section of the table 1820. The retaining table 1820 includes a plate 1824 having a generally flat top surface with opposed first and second ends 1825a, 1825b and opposed first and second lateral edges 1827a, 1827b for supporting a disposable container. The table 1820 includes a door 1845 connected to the plate 1824 by at least one hinge 1841 along the first lateral edge 1827a and being movable between open and closed positions, and a latch 1846 to releasably retain the door 1845 in the closed position disposed along the opposed second lateral edge 1827b. The table 1820 also includes example openings 1843 and 1853 at the first and second ends 1825a, 1825b of the plate 1824, respectively, configured for pass through of components extending from the disposable container, such as tubings. However, it will be appreciated that suitable openings to permit pass through of tubings extending from a container may be provided in alternative configurations, such as in the ends of the door.

The door may optionally include a second plate 1823 connected to the door 1845 and biased toward the plate 1824 of the table 1820 when the door 1845 is in the closed position. The second plate 1823 is connected to the door 1845 by a plurality of springs 1835, 1837, 1839. When the door is in a closed position, the springs cause the second plate 1823 to be biased toward a container that would be disposed on the plate 1824. The second plate 1823 may press against the container 1821 to help spread the fluid throughout the container and reduce sloshing during oscillation or other movement of the table and/or to keep the bag in close contact with the top surface of the plate to improve thermal conduction or benefit other processes associated with alternative apparatus provided on the top surface of the plate.

The door 1845 and plate 1823 may be solid and optionally may be clear, to permit the disposable container to be viewed while the door 1845 is in a closed position. The embodiment may include alternatively configured hinge/latch connectors for the door. Multiple tubings 1848, 1849, 1850 are shown, for example, extending from first and second ends of the disposable container 1821, which may pass through openings 1843 and 1853. It will be appreciated that more or fewer tubings may extend from disposable container.

Thus, retaining tables for use in a system for processing (e.g., concentrating or washing) small volumes of biological cells have been disclosed. The description provided above, and the other aspects provided below, are intended for illustrative purposes, and are not intended to limit the scope of the disclosure to any particular method, system, apparatus or device described herein.

It will be understood that the embodiments and examples described above are illustrative of some of the applications of the principles of the present subject matter. Numerous modifications may be made by those skilled in the art without departing from the spirit and scope of the claimed subject matter, including combinations of features that are individually disclosed or claimed herein. For these reasons, the scope of the disclosure is not limited to the above description, and it is understood that claims may be directed to the features disclosed herein, including as combinations of features that are individually disclosed or claimed herein.

Other Aspects

Aspect 1. A retaining table for use with a fluid processing system comprising: a plate having a generally flat top surface with opposed first and second ends and opposed first and second lateral edges for supporting a disposable container; a first retaining structure connected to the plate along the first end, and a second retaining structure connected to the plate along the second end.

Aspect 2. The retaining table of Aspect 1, wherein the first retaining structure further comprises a clip including a base and a mobile jaw pivotally connected to the base, with the base being fixedly or adjustably connected to the plate.

Aspect 3. The retaining table of Aspect 2, wherein the clip further comprises a biasing element that biases the mobile jaw to a closed position.

Aspect 4. The retaining table of Aspect 2, wherein the clip further comprises at least one protrusion on at least one of the mobile jaw and the base.

Aspect 5. The retaining table of Aspect 2, wherein the clip further comprises at least one of the mobile jaw and the base having at least one protrusion and the other of the mobile jaw and base having at least one recess that receives the at least one protrusion.

Aspect 6. The retaining table of Aspect 2, wherein a mating surface of at least one of the mobile jaw and base further comprises a compliant material.

Aspect 7. The retaining table of Aspect 1, further comprising at least one retaining structure connected to the plate along at least one of the first and second lateral edges.

Aspect 8. The retaining table of Aspect 7, wherein the at least one retaining structure connected to the plate along at least one of the first and second lateral edges further comprises a barrier extending upward from the plate.

Aspect 9. The retaining table of Aspect 8, wherein the first retaining structure is adjustably connected to two barriers along the respective first and second lateral edges of the plate.

Aspect 10. The retaining table of Aspect 9, further comprising a clamp system connected to the first retaining structure and releasably lockable along the two barriers.

Aspect 11. The retaining table of Aspect 10, wherein the clamp system comprises: a first clamp device slidably and lockingly connected to the barrier along the first lateral edge of the plate; a second clamp device slidably and lockingly connected to the barrier along the second lateral edge of the plate; and each clamp device comprising a base and a latch that engages the respective barrier.

Aspect 12. The retaining table of Aspect 11, wherein each clamp device is biased to a locked position relative to the respective barrier to which it is slidably and lockingly connected.

Aspect 13. The retaining table of Aspect 11, wherein each clamp device includes a release mechanism further comprising a movable latch, button or thumb screw.

Aspect 14. The retaining table of Aspect 1, wherein the second retaining structure further comprises a bar connected to the plate.

Aspect 15. The retaining table of Aspect 14, wherein the bar has a first end connected to the plate and a second end spaced above and parallel to or angled away from the plate.

Aspect 16. The retaining table of Aspect 1, wherein the first retaining structure further comprises an upstanding portion configured as a post or elongated projection having an enlarged head.

Aspect 17. The retaining table of Aspect 1, wherein the first retaining structure further comprises a bar having a portion of the bar spaced from the plate.

Aspect 18. The retaining table of Aspect 17, further comprising a cam disposed on the bar and configured to engage the disposable container.

Aspect 19. The retaining table of Aspect 17, wherein the first retaining structure further comprises a releasable locking system including the bar being configured as a mobile bar connected at first and second ends to the plate.

Aspect 20. The retaining table of Aspect 19, wherein the first end of the mobile bar is pivotally connected to the plate and the second end of the mobile bar is releasably connected to the plate.

Aspect 21. The retaining table of Aspect 20, wherein the second end of the mobile bar is releasably engaged by a pin that is movably connected to a stationary block that is connected to the plate.

Aspect 22. The retaining table of Aspect 16, wherein the second end of the mobile bar further comprises a locking mechanism including at least one protrusion at the second end of the mobile bar and an aperture through the plate configured to releasably receive the at least one protrusion.

Aspect 23. The retaining table of Aspect 1, wherein the first retaining structure further comprises a band extending from the first lateral edge to the second lateral edge.

Aspect 24. The retaining table of Aspect 1, wherein the second retaining structure further comprises a second band extending from the first lateral edge to the second lateral edge.

Aspect 25. The retaining table of Aspect 17, wherein the bar of the first retaining structure is stationary and the table further comprises a roller spaced apart from the stationary bar.

Aspect 26. The retaining table of Aspect 25, wherein the roller is pivotally connected to the plate at a first end and releasably connected to the plate at a second end.

Aspect 27. The retaining table of Aspect 25, wherein the roller is connected to the stationary bar by springs and is configured to move toward and away from the second end of the plate.

Aspect 28. The retaining table of claim 1, wherein the table is configured for movement.

Aspect 29. The retaining table of claim 28, wherein the table has an axis of rotation that is perpendicular to the lateral edges of the plate and the table is configured to be connected to a drive shaft that imparts oscillation.

Aspect 30. The retaining table of claim 1, wherein the plate includes a temperature adjusting element for cooling or heating the disposable container.

Aspect 31. A retaining table for use with a fluid processing system comprising: a plate having a generally flat top surface with opposed first and second ends and opposed first and second lateral edges for supporting a disposable container; a door connected to the plate by at least one hinge along the first lateral edge and being movable between open and closed positions, and a latch along the opposed second lateral edge releasably retains the door in the closed position; and further comprising openings at the first and second ends of the plate or door configured for pass through of components extending from the disposable container.

Aspect 32. The retaining table of Aspect 31, further comprising a second plate connected to the door and biased toward the plate of the table when the door is in the closed position.

Aspect 33. The retaining table of Aspect 32, wherein the second plate is connected to the door by a plurality of springs.

Aspect 34. The retaining table of Aspect 33, wherein the second plate is configured to engage the disposable container.

Aspect 35. The retaining table according to Aspect 7, wherein the at least one retaining structure connected to the plate along at least one of the first and second lateral edges further comprises a barrier configured as a raised wall.

Aspect 36. The retaining table according to Aspect 7, wherein the at least one retaining structure connected to the plate along at least one of the first and second lateral edges is adjustable.

Aspect 37. The retaining table according to Aspect 7, wherein the at least one retaining structure connected to the plate along at least one of the first and second lateral edges includes a notched portion.

Aspect 38. The retaining table of Aspect 10, wherein the clamp system further comprises a yoke to which a first clamp device, a second clamp device and the first retaining structure are connected.

Aspect 39. The retaining table of Aspect 10, wherein the clamp system further comprises first and second clamp devices, each of which further comprises a stationary base and a latch biased to a locking position Aspect 40. The retaining table of Aspect 39, wherein each clamp device further comprises a lever configured to move the latch Aspect 41. The retaining table of Aspect 40, wherein the lever of each clamp device provides a release mechanism.

Aspect 42. The retaining table of Aspect 2, wherein the clip includes an exposed handle on the mobile jaw.

Aspect 43. The retaining table of Aspect 5, wherein the protrusion is on the mobile jaw and the recess is on the stationary base of the clip.

Aspect 44. The retaining table of Aspect 5, wherein the protrusion is on the stationary base and the recess is on the mobile jaw of the clip.

Aspect 45. The retaining table of Aspect 4, wherein at least a portion of the at least one protrusion has a triangular, rectangular or pentagonal shape.

Aspect 46. The retaining table of Aspect 5, wherein the clip includes at least three protrusions, preferably alternating between mating faces of the mobile jaw and base.

Aspect 47. A retaining table for use with a fluid processing system comprising: a plate having a generally flat top surface with opposed first and second ends and opposed first and second lateral edges for supporting a disposable container; and a band along a first end of the plate extending from the first lateral edge to the second lateral edge.

Aspect 48. The retaining table of Aspect 47, further comprising a bar along the second end of the plate.

Aspect 49. The retaining table of Aspect 47, further comprising at least one barrier along at least one lateral edge of the plate.

Aspect 50. A retaining table of Aspect 47, further comprising a second band along a second end of the plate extending from the first lateral edge to the second lateral edge.

Aspect 51. A retaining table for use with a fluid processing system comprising: a plate having a generally flat top surface with opposed first and second ends and opposed first and second lateral edges for supporting a disposable container; and a stationary bar along a first end of the plate.

Aspect 52. The retaining table of Aspect 51, further comprising a second bar along the second end of the plate.

Aspect 53. The retaining table of Aspect 51, further comprising at least one barrier along at least one lateral edge of the plate.

Aspect 54. The retaining table of Aspect 51, further comprising a roller along the first end of the plate, spaced apart from the stationary bar.

Aspect 55. The retaining table of Aspect 54, wherein the roller is pivotally connected to the plate at a first end with a hinge and the second end with a locking system.

Aspect 56. The retaining table of Aspect 51, wherein a roller is connected to the first end of the plate by springs and is configured to move toward and away from the second end of the plate.

Aspect 57. The retaining table of Aspect 56, wherein the connection of the springs to the first end of the plate further comprises the springs being connected to the stationary bar at the first end of the plate.

The invention claimed is:

1. A retaining table for use with a fluid processing system comprising:
    a plate having a generally flat top surface with opposed first and second ends and opposed first and second lateral edges for supporting a disposable container;
    a first retaining structure connected to the plate along the first end, and
    a second retaining structure connected to the plate along the second end; and
    wherein the first retaining structure further comprises a clip including a base and a mobile jaw pivotally connected to the base, with the base being connected to the plate.

2. The retaining table of claim 1, wherein the clip further comprises a biasing element that biases the mobile jaw to a closed position.

3. The retaining table of claim 1, wherein the clip further comprises at least one protrusion on at least one of the mobile jaw and the base.

4. The retaining table of claim 1, wherein the clip further comprises at least one of the mobile jaw and the base having at least one protrusion and the other of the mobile jaw and base having at least one recess that receives the at least one protrusion.

5. The retaining table of claim 1, wherein a mating surface of at least one of the mobile jaw and base further comprises a compliant material.

6. The retaining table of claim 1, further comprising at least one retaining structure connected to the plate along at least one of the first and second lateral edges.

7. The retaining table according to claim 6, wherein the at least one retaining structure connected to the plate along at least one of the first and second lateral edges further comprises a barrier extending upward from the plate.

8. A retaining table for use with a fluid processing system comprising:

a plate having a generally flat top surface with opposed first and second ends and opposed first and second lateral edges for supporting a disposable container;
a first retaining structure connected to the plate along the first end, and
a second retaining structure connected to the plate along the second end; and
wherein the first retaining structure is connected to two barriers extending upward from the plate along the respective first and second lateral edges of the plate.

9. The retaining table according to claim 8, further comprising a clamp system connected to the first retaining structure and releasably lockable along the two barriers.

10. The retaining table of claim 9, wherein the clamp system comprises:
a first clamp device slidably and lockingly connected to the barrier along the first lateral edge of the plate;
a second clamp device slidably and lockingly connected to the barrier along the second lateral edge of the plate; and
each clamp device comprising a base and a latch that engages the respective barrier.

11. The retaining table of claim 10, wherein the latch of each respective clamp device is biased to a locked position relative to the respective barrier to which the respective clamp device is slidably and lockingly connected.

12. The retaining table of claim 10, wherein each clamp device includes a release mechanism with each latch further comprising a movable latch, button or thumb screw.

13. The retaining table of claim 1, wherein the second retaining structure further comprises a bar connected to the plate with the bar having a portion of the bar spaced from the plate.

14. The retaining table of claim 13, wherein the bar has a first end connected to the plate and a second end spaced above and parallel to or angled away from the plate.

15. A retaining table for use with
a fluid processing system comprising:
a plate having a generally flat top surface with opposed first and second ends and opposed first and second lateral edges for supporting a disposable container;
a first retaining structure connected to the plate along the first end, and
a second retaining structure connected to the plate along the second end;
wherein the first retaining structure further comprises an upstanding portion configured as a post or elongated projection having an enlarged head; and
wherein the second retaining structure further comprises a bar connected to the plate with the bar having a portion of the bar spaced from the plate.

16. A retaining table for use with a fluid processing system comprising:
a plate having a generally flat top surface with opposed first and second ends and opposed first and second lateral edges for supporting a disposable container;
a first retaining structure connected to the plate along the first end, and
a second retaining structure connected to the plate along the second end; and
wherein the first retaining structure further comprises a bar having a portion of the bar spaced from the plate.

17. The retaining table of claim 16, further comprising a cam disposed on the bar and configured to engage the disposable container.

18. The retaining table of claim 16, wherein the first retaining structure further comprises a releasable locking system including the bar being configured as a mobile bar connected at first and second ends to the plate.

19. The retaining table of claim 18, wherein the first end of the mobile bar is pivotally connected to the plate and the second end of the mobile bar is releasably connected to the plate.

20. The retaining table of claim 19, wherein the second end of the mobile bar is releasably engaged by a pin that is movably connected to a stationary block that is connected to the plate.

21. The retaining table of claim 20, wherein the second end of the mobile bar further comprises a locking mechanism including at least one protrusion at the second end of the mobile bar and an aperture through the plate configured to releasably receive the at least one protrusion.

22. A retaining table for use with a fluid processing system comprising:
a plate having a generally flat top surface with opposed first and second ends and opposed first and second lateral edges for supporting a disposable container;
a first retaining structure connected to the plate along the first end, and
a second retaining structure connected to the plate along the second end; and
wherein the first retaining structure further comprises a band extending across the plate along the first end from the first lateral edge to the second lateral edge.

23. The retaining table of claim 22, wherein the second retaining structure further comprises a second band extending across the plate along the second end from the first lateral edge to the second lateral edge.

24. The retaining table of claim 16, wherein the bar of the first retaining structure is stationary and the table further comprises a roller spaced apart from the stationary bar.

25. The retaining table of claim 24, wherein the roller is pivotally connected to the plate at a first end and releasably connected to the plate at a second end.

26. The table of claim 24, wherein the roller is connected to the stationary bar by springs and is configured to move toward and away from the second end of the plate.

27. The retaining table of claim 1, wherein the table is configured for movement.

28. The retaining table of claim 27, wherein the table has an axis of rotation that is perpendicular to the lateral edges of the plate and the table is configured to be connected to a drive shaft and drive shaft coupling that impart oscillation upon rotation of the drive shaft.

29. A retaining table for use with a fluid processing system comprising:
a plate having a generally flat top surface with opposed first and second ends and opposed first and second lateral edges for supporting a disposable container;
a first retaining structure connected to the plate along the first end, and
a second retaining structure connected to the plate along the second end; and
wherein the plate includes a temperature adjusting element connected to the plate and which is configured to emit a lowered or increased temperature for cooling or heating the disposable container.

30. A retaining table for use with a fluid processing system comprising:
a plate having a generally flat top surface with opposed first and second ends and opposed first and second lateral edges for supporting a disposable container;
a door connected to the plate by at least one hinge along the first lateral edge and being movable between open and closed positions, and a latch along the opposed second lateral edge releasably retains the door in the closed position; and further comprising openings at the first and second ends of the plate or door configured for pass through of components extending from the disposable container; and further comprising a second plate connected to and extending from the door and is spaced from the plate of the table when the door is in the closed position over the plate of the table.

31. The retaining table of claim 30, wherein the second plate is connected to and extending from the door via a plurality of biasing elements by which the second plate is biased toward the plate of the table when the door is in the closed position over the plate of the table.

32. The retaining table of claim 31, wherein the plurality of biasing elements by which the second plate is connected to the door further comprises a plurality of springs.

* * * * *